(12) United States Patent
Kim

(10) Patent No.: US 9,897,557 B2
(45) Date of Patent: Feb. 20, 2018

(54) X-RAY PHOTOGRAPHING APPARATUS AND METHOD OF OPERATING THE SAME

(71) Applicant: SAMSUNG ELECTRONICS CO., LTD., Suwon-si (KR)

(72) Inventor: Jong-pil Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 47 days.

(21) Appl. No.: 14/316,016

(22) Filed: Jun. 26, 2014

(65) Prior Publication Data
US 2015/0003589 A1  Jan. 1, 2015

(30) Foreign Application Priority Data
Jun. 26, 2013 (KR) .................. 10-2013-0073974

(51) Int. Cl.
| | | |
|---|---|---|
| *G01N 23/04* | (2006.01) | |
| *A61B 6/04* | (2006.01) | |
| *A61B 6/08* | (2006.01) | |
| *A61B 6/00* | (2006.01) | |
| *A61B 6/02* | (2006.01) | |
| *H01J 35/06* | (2006.01) | |

(52) U.S. Cl.
CPC ......... *G01N 23/046* (2013.01); *A61B 6/0414* (2013.01); *A61B 6/08* (2013.01); *A61B 6/4007* (2013.01); *A61B 6/4233* (2013.01); *A61B 6/502* (2013.01); *A61B 6/544* (2013.01); *A61B 6/02* (2013.01); *A61B 6/4266* (2013.01); *A61B 6/482* (2013.01); *H01J 35/065* (2013.01)

(58) Field of Classification Search
CPC ........ A61B 6/502; A61B 6/0414; A61B 6/025
See application file for complete search history.

(56) References Cited

U.S. PATENT DOCUMENTS

| | | | | |
|---|---|---|---|---|
| 4,719,645 A | * | 1/1988 | Yamabe ................. | H01J 35/10 378/124 |
| 6,480,565 B1 | | 11/2002 | Ning | |
| 7,359,484 B2 | | 4/2008 | Qiu et al. | |
| 7,431,500 B2 | | 10/2008 | Deych et al. | |

(Continued)

FOREIGN PATENT DOCUMENTS

| | | |
|---|---|---|
| DE | 10332301 A1 | 2/2005 |
| EP | 2184007 A1 | 5/2010 |

(Continued)

OTHER PUBLICATIONS

Communication dated Nov. 14, 2014, issued by the European Patent Office in counterpart European Application No. 14173868.2.

(Continued)

*Primary Examiner* — Hoon Song
(74) *Attorney, Agent, or Firm* — Sughrue Mion, PLLC

(57) ABSTRACT

An X-ray photographing apparatus and a method of operating the X-ray photographing method are disclosed. The X-ray photographing apparatus includes a plurality of X-ray generators configured to generate an X-ray; a plurality of X-ray detectors facing the plurality of X-ray generators and configured to detect X-rays that are transmitted through an object; and a plurality of sensors, which are provided between the plurality of X-ray generators and the plurality of X-ray detectors, and which are configured to sense the object.

19 Claims, 22 Drawing Sheets

(56) References Cited

U.S. PATENT DOCUMENTS

| | | | |
|---|---|---|---|
| 7,496,176 B2 | 2/2009 | Aslund | |
| 7,767,990 B2 * | 8/2010 | Cadwalader | A61B 6/107 |
| | | | 128/846 |
| 7,864,917 B2 | 1/2011 | Ribbing et al. | |
| 7,978,816 B2 | 7/2011 | Matsuura et al. | |
| 7,991,120 B2 | 8/2011 | Okunuki et al. | |
| 2007/0165781 A1 | 7/2007 | Aslund | |
| 2008/0224047 A1 * | 9/2008 | Nakayama | A61B 6/107 |
| | | | 250/354.1 |
| 2008/0279330 A1 * | 11/2008 | Ueki | A61B 5/0091 |
| | | | 378/63 |
| 2009/0143664 A1 | 6/2009 | Oelschlegel et al. | |
| 2009/0290679 A1 * | 11/2009 | Mikami | A61B 6/0414 |
| | | | 378/37 |
| 2009/0323893 A1 * | 12/2009 | Hanke | A61B 6/502 |
| | | | 378/37 |
| 2010/0246759 A1 * | 9/2010 | Ogura | A61B 6/025 |
| | | | 378/21 |
| 2011/0069808 A1 | 3/2011 | DeFreitas et al. | |
| 2011/0075809 A1 | 3/2011 | Boese et al. | |
| 2012/0008739 A1 | 1/2012 | Hoernig et al. | |
| 2012/0018641 A1 | 1/2012 | Watanabe et al. | |
| 2012/0051501 A1 | 3/2012 | Nakayama | |
| 2012/0051522 A1 | 3/2012 | Nishino et al. | |
| 2012/0310079 A1 | 12/2012 | Henning | |
| 2013/0028499 A1 | 1/2013 | Tsujii et al. | |
| 2014/0016749 A1 * | 1/2014 | Oda | A61B 6/5258 |
| | | | 378/62 |
| 2015/0117601 A1 * | 4/2015 | Keeve | A61B 6/589 |
| | | | 378/41 |

FOREIGN PATENT DOCUMENTS

| | | |
|---|---|---|
| EP | 2986226 | 10/2014 |
| EP | 2818113 A1 | 12/2014 |
| EP | 2819145 A1 | 12/2014 |
| JP | 2009-297314 A | 12/2009 |
| KR | 10-0933118 B1 | 12/2009 |
| KR | 10-2012-0108843 A | 10/2012 |
| WO | 2007/111669 A2 | 10/2007 |
| WO | 2014/167097 A1 | 10/2014 |

OTHER PUBLICATIONS

Communication dated Nov. 29, 2016, from the European Patent Office in counterpart European Application No. 14173868.2.

Communication dated Oct. 20, 2017, issued by the European Patent Office in counterpart European Patent Application No. 14173868.2.

* cited by examiner

X-RAY PHOTOGRAPHING APPARATUS AND METHOD OF OPERATING THE SAME

CROSS-REFERENCE TO RELATED APPLICATION

This application claims the benefit of Korean Patent Application No. 10-2013-0073974, filed on Jun. 26, 2013, in the Korean Intellectual Property Office, the disclosure of which is incorporated herein in its entirety by reference.

BACKGROUND

1. Field

One or more exemplary embodiments relate to an X-ray photographing apparatus using an X-ray and a method of operating the X-ray photographing apparatus.

2. Description of the Related Art

X-rays are used in non-destructive testing, structural and physical properties testing, image diagnosis, security inspection, and the like in the fields of industry, science, medical treatment, etc. Generally, an imaging system using X-rays for such purposes includes an X-ray generator for radiating an X-ray and an X-ray detector for detecting X-rays that have passed through an object.

The X-ray detector is being rapidly converted from a film device to a digital device, whereas the X-ray generator uses an electron generation device having a tungsten filament type cathode. Thus, a single electron generation device is mounted in a single X-ray photographing apparatus. The X-ray detector is generally implemented as a flat panel type, which is problematic in that there is a distance between the X-ray generator and the object when obtaining an image using the single electron generation device. Furthermore, the object needs to be photographed by using a single X-ray generator, which may make it impossible to select and photograph a specific part of the object.

SUMMARY

One or more exemplary embodiments provide an X-ray photographing apparatus including a flat panel type X-ray generator and a method of operating the X-ray photographing apparatus.

One or more exemplary embodiments further provide an X-ray photographing apparatus capable of obtaining a tomography image and a method of operating the X-ray photographing apparatus.

One or more exemplary embodiments further provide an X-ray generator capable of adjusting a radiation angle of an X-ray, an X-ray photographing apparatus including the X-ray generator, and a method of operating the X-ray photographing apparatus.

One or more exemplary embodiments further provide an X-ray photographing apparatus for detecting an object and radiating an X-ray only to the object and a method of operating the X-ray photographing apparatus.

Additional aspects will be set forth in part in the description which follows and, in part, will be apparent from the description, or may be learned by practice of the presented exemplary embodiments.

According to an aspect of an exemplary embodiment, there is provided an X-ray photographing apparatus including: a plurality of X-ray generators configured to generate an X-ray; a plurality of X-ray detectors facing the plurality of X-ray generators and configured to detect X-rays that are transmitted through the object; and a plurality of sensors, which are provided between the plurality of X-ray generators and the plurality of X-ray detectors, and which are configured to sense the object.

An X-ray generator corresponding to a location of the object, among the plurality of X-ray generators, may be configured to generate the X-ray.

An X-ray detector corresponding to a location of the object, among the plurality of X-ray detectors, may be configured to detect the X-ray.

The plurality of X-ray generators and the plurality of X-ray detectors may be provided in one dimension or in two dimensions.

Each of the plurality of sensors may be configured to sense the object.

The X-ray photographing apparatus may further include: a controller configured to determine a location of the object by using results of sensing by the plurality of sensors.

At least one of the plurality of sensors may be disposed in a region that does not overlap with the plurality of X-ray generators.

The X-ray photographing apparatus may further include: a panel that is provided between the plurality of X-ray generators and the plurality of X-ray detectors and that is configured to contact the object.

The plurality of sensors may be provided on the panel.

The panel may be configured to compress the object.

At least one of the plurality of sensors may include a light sensor or a touch sensor.

The light sensor may include an illumination sensor.

The plurality of X-ray generators may be configured to move away from or closer to the object.

Each of the plurality of X-ray generators may include: an electron emission device configured to emit electrons; and an anode electrode configured to emit X-rays using the electrons emitted by the electron emission device.

At least one of the plurality of sensors may be disposed on a same plane as the anode electrode.

According to another aspect of an exemplary embodiment, there is provided an X-ray photographing method performed by an X-ray photographing apparatus, the X-ray photographing method including: sensing an object; generating an X-ray by using an X-ray generator corresponding to a location of the object, from among a plurality of X-ray generators; and detecting the X-ray transmitted through the object by using an X-ray detector corresponding to the location of the object, from among a plurality of X-ray detectors.

The plurality of X-ray generators and the plurality of X-ray detectors may be provided in one dimension or in two dimensions.

The X-ray photographing method may further include: determining the location of the object by using a result of the sensing.

The detecting may be performed by using at least one of a light sensor and a touch sensor.

The generating of the X-ray may include: in response to determining that an X-ray generation area is smaller than a test area of the object, moving the plurality of X-ray generators horizontally with respect to the object to transmit the X-ray to the test area of the object.

According to an aspect of an exemplary embodiment, there is provided an X-ray apparatus including: a plurality of X-ray detectors configured to detect X-rays transmitted through an object; and a panel comprising a plurality of sensors configured to sense a location of the object on the panel, wherein the X-rays are generated by an X-ray generator according to the sensed location of the object.

The panel is provided between the plurality of X-ray detectors and an X-ray generator.

The X-rays are generated by the X-ray generator which corresponds to the sensed location of the object, the X-ray generator being selected from among a plurality of X-ray generators.

The plurality of sensors are formed of a transparent material.

The plurality of sensors are implemented as a touch pad.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
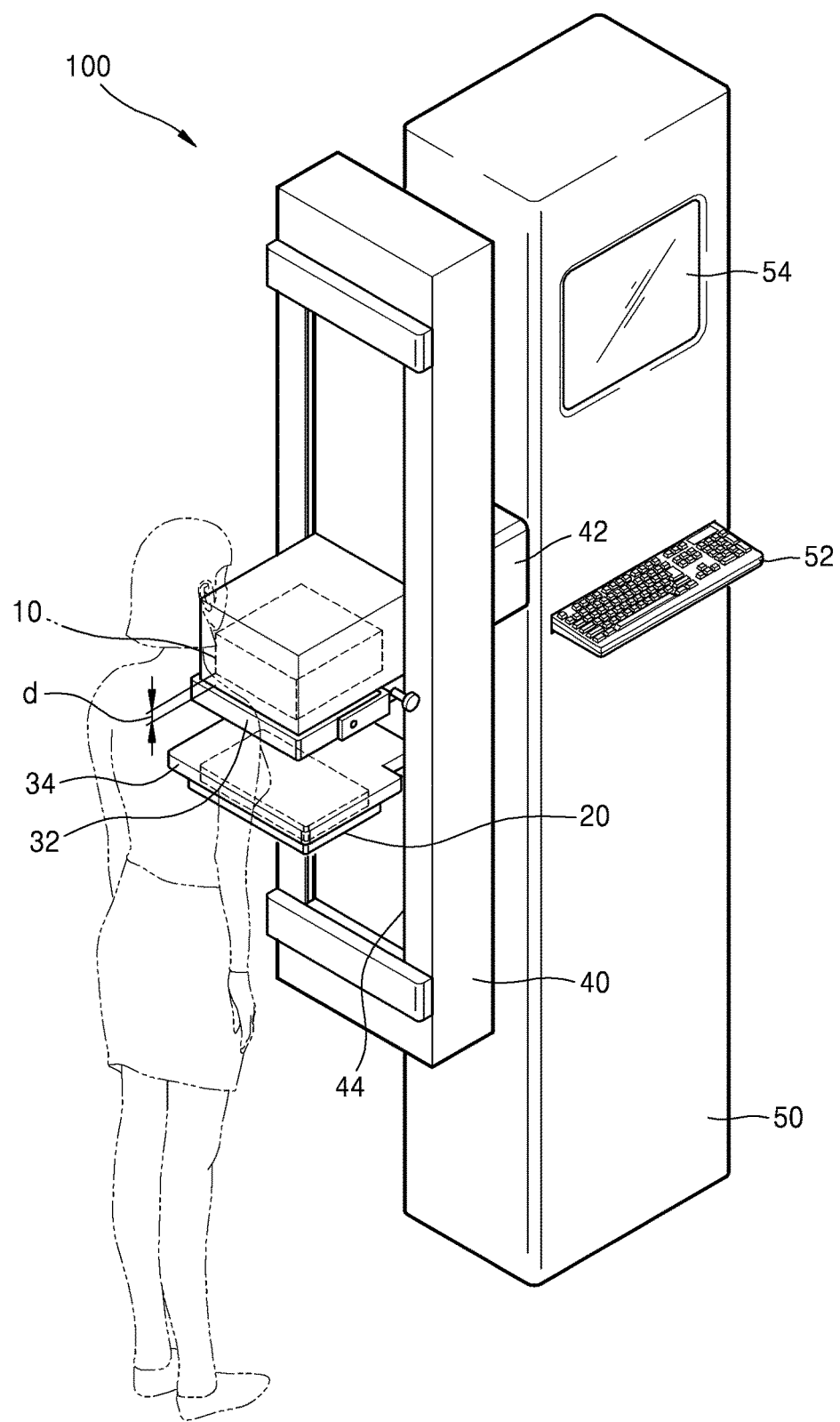
FIG. 1 is a schematic perspective view of an X-ray photographing apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Also, the thickness or size of each element illustrated in the drawings may be exaggerated for convenience of explanation and clarity. Accordingly, the exemplary embodiments are merely described below, by referring to the figures, to explain aspects of the present description.

The attached drawings for illustrating exemplary embodiments are referred to in order to gain a sufficient understanding of the exemplary embodiments, the merits thereof, and the objectives accomplished by the implementation of the exemplary embodiments. The exemplary embodiments may, however, be embodied in many different forms and should not be construed as being limited to the exemplary embodiments set forth herein; rather, these exemplary embodiments are provided such that this disclosure will be thorough and complete, and will fully convey the concept of the exemplary embodiments to one of ordinary skill in the art.

Hereinafter, the terms used in the specification will be briefly described, and then the exemplary embodiments will be described in detail.

The terms used in this specification are those general terms currently widely used in the art in consideration of functions in regard to the exemplary embodiments, but the terms may vary according to the intention of those of ordinary skill in the art, precedents, or new technology in the art. Also, specified terms may be selected by the applicant, and in this case, the detailed meaning thereof will be described in the detailed description. Thus, the terms used in the specification should be understood not as simple names but based on the meaning of the terms and the overall description of the exemplary embodiments.

In the present specification, an object may include a human being or an animal, or a part of the human being or the animal. For example, the object may include organs, such as the liver, the heart, the uterus, the brain, breasts, the abdomen, or blood vessels. In the present specification, a "user" is a medical expert, for example, a doctor, a nurse, a medical specialist, and a medical imaging expert, or an engineer managing medical apparatuses; however, the exemplary embodiments are not limited thereto.

Expressions such as "at least one of," when preceding a list of elements, modify the entire list of elements and do not modify the individual elements of the list.

FIG. 1 is a schematic perspective view of an X-ray photographing apparatus 100 according to an exemplary embodiment. The X-ray photographing apparatus 100 of FIG. 1 is exemplarily shown as a mammography apparatus that photographs a breast, but the X-ray photographing apparatus 100 is not limited thereto. The X-ray photographing apparatus 100 of the may be applied to an X-ray photographing apparatus that contacts an object and generates an X-ray.

Referring to FIG. 1, the X-ray photographing apparatus 100 includes an X-ray generator 10 that generates the X-ray, an X-ray detector 20 that detects the X-ray that is transmitted to an object 200, and panels 32 and 34 that may contact the object 200. The X-ray photographing apparatus 100 may further include a gantry 40 that supports the X-ray generator 10, the X-ray detector 20, and the panels 32 and 34, and a main body 50 that supports the gantry 40.

The main body 50 may include a user input device 52 that may input a user command to operate the X-ray photographing apparatus 100, a processor (not shown) that generates an image corresponding to the transmitted X-ray, a display 54 that displays the generated image, and a controller (not shown) that controls general operations of the X-ray photographing apparatus 100. The user input device 52, the processor (not shown), the display 54, and the controller (not shown) may not be necessarily included in the main body 50, and may instead be implemented as external devices that may communicate with the X-ray photographing apparatus 100 by wire or wirelessly.

The gantry 40 may be fixed to the main body 50 via a gantry driver 42. The gantry 40 may be disposed in one side surface of the main body 50 longitudinally. The gantry driver 42 may rotate the gantry 40 by 360° or at an angle. In addition, the gantry driver 42 may operate to move the gantry 40 up and down longitudinally with respect to the main body 50. Thus, the gantry driver 42 may move the gantry 40 up or down longitudinally with respect to the main body 50 so that a height of the gantry 40 may be adjusted in accordance with the object 200. Further, the gantry driver 42 may rotate the gantry 42.

The panels 32 and 34 that may contact the object 200 may be disposed on the front of the gantry 40. The first and second panels 32 and 34 may move up and down by using a guide groove 44 that is longitudinally included in the front of the gantry 40. Thus, if the object 200, for example, breasts of a patient, is placed between first and second panels 32 and 34, at least one of the first and second panels 32 and 34 may press the object 200 to compress the object 200. For example, the second panel 34 may be moved up or down to allow the object 200 to be seated on the second panel 34 and then the first panel 32 may be moved down to press the object 200 and compress the object 200.

The X-ray generator 10 that generates the X-ray may be disposed on the first panel 32. The X-ray generator 10 may be moved far away from or closer to the object 200 while maintaining a distance d with the first panel 32. For example, the X-ray generator 10 may be integrated with the first panel 32 so that the X-ray generator 10 and the first panel 32 may move along the guide groove 44.

In more detail, when the first panel 32 presses the object 200, since the X-ray generator 10 radiates the X-ray to the object 200, a distance between the X-ray generator 10 and the object 200 may be minimized. For example, the distance between the X-ray generator 10 and the object 200 may be about 10 cm. Thus, radiation of the X-ray to a region other than the object 200 may be prevented, thereby minimizing an X-ray radiation dose. To minimize the distance between the X-ray generator 10 and the object 200, the X-ray generator 10 may be disposed to contact a top side of the object 200. The X-ray generator 10 includes a plurality of X-ray generation units 300, which will be described later.

The X-ray detector 20 that detects the X-ray that is transmitted to the object 200 may be provided under the second panel 34. The X-ray detector 20 may be moved far away from or closer to the object 200 while maintaining a distance d with the second panel 34. For example, the X-ray detector 20 may be integrated with the second panel 34 so that the X-ray detector 20 and the second panel 34 may move along the guide groove 44.

In more detail, when the object 200 is seated on the second panel 34, since the X-ray detector 20 detects the X-ray that is transmitted to the object 200, a distance between the X-ray detector 20 and the object 200 may be minimized. Thus, the X-ray may be more exactly detected. To minimize the distance between the X-ray detector 20 and the object 200, the X-ray detector 20 may be disposed to contact a bottom side of the object 200. The X-ray detector 20 includes a plurality of X-ray detection units, which will be described later.

Figure 2A:
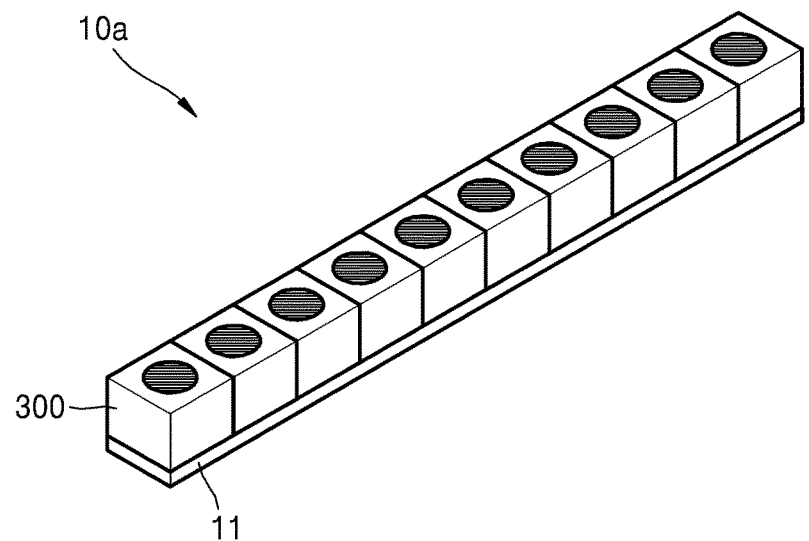
FIGS. 2A and 2B are schematic diagrams of X-ray generators including a plurality of X-ray generation units according to an exemplary embodiment.
Figure 2B:
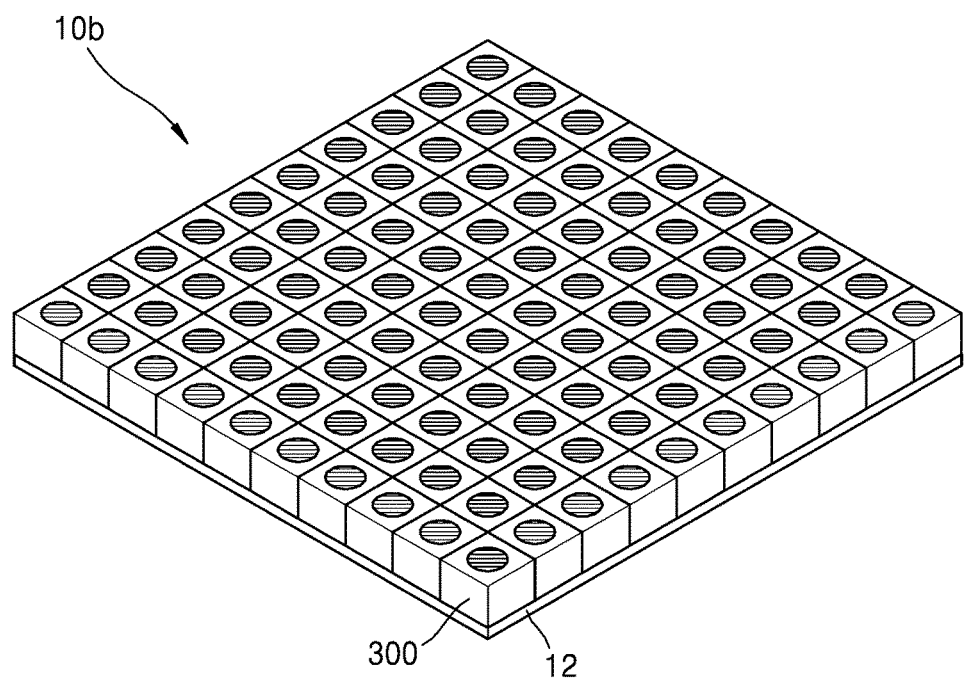

The X-ray generator 10 will now be described in more detail below. FIGS. 2A and 2B are schematic diagrams of X-ray generators 10a and 10b including the plurality of X-ray generation units 300 according to an exemplary embodiment. Referring to FIG. 2A, the X-ray generator 10a may include the X-ray generation units 300 provided in one dimension. Referring to FIG. 2B, the X-ray generator 10b may include the X-ray generation units 300 provided in two dimensions.

Each of the X-ray generation units 300 may be independently driven to generate an X-ray. Accordingly, all of the X-ray generation units 300 may be driven to radiate X-rays to the object 200 or, alternatively, some of the X-ray generation units 300 may be driven to radiate X-rays to the object 200. At least one of the X-ray generation units 300 may radiate X-rays to all regions of the object 200 or a specific region. In addition, at least one of the X-ray generation units 300 may be simultaneously or sequentially driven. In this case, only some X-ray detection units corresponding to the X-ray generation units 300 that are being driven may be driven.

Although the X-ray generation units 300 are respectively formed on a single substrate 11 and 12 as shown in FIGS. 2A and 2B, the exemplary embodiments are not limited thereto. Each of the X-ray generation units 300 may be separately manufactured and the X-ray generation units 300 may be assembled into the X-ray generators 10a and 10b. Alternatively, some of the X-ray generation units 300 may be formed on a single substrate and then assembled together with other X-ray generation units 300 formed on other substrates. For example, an X-ray generator in two dimensions may be manufactured by generating X-ray generators in one dimension on a single substrate and arranging the X-ray generators in one dimension. Although not shown, an X-ray controller for controlling a proceeding path of an X-ray generated by each of the X-ray generation units 300 such that the X-ray does not interfere with a neighboring X-ray may be provided. In the X-ray control unit, an opening is formed in an area corresponding to each of the X-ray generation units 300 and an X-ray absorbing material may be formed in a grid type device in the other area (for example, a boundary area between the neighboring X-ray generation units 300).

Figure 3A:
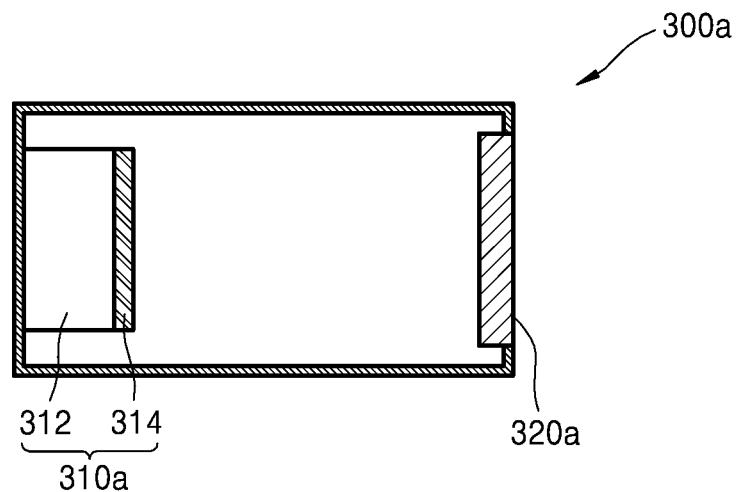
FIGS. 3A to 3D are schematic diagrams of X-ray generation units according to exemplary embodiments.

FIGS. 3A to 3D are schematic diagrams of X-ray generation units (e.g., X-ray generators) 300a, 300b, 300c, and 300d according to exemplary embodiments. Referring to FIG. 3A, the X-ray generation unit 300a may include an electron emission device 310a that may emit electrons and an anode electrode 320a that may emit an X-ray by collision of the emitted electrons. The anode electrode 320a may include metal or a metal alloy such as W, Mo, Ag, Cr, Fe, Co, Cu, etc.

The electron emission device 310a may include a cathode electrode 312 and an electron emission source 314 that emits electrons and that is provided on the cathode electrode 312. The cathode electrode 312 may be metal such as Ti, Pt, Ru, Au, Ag, Mo, Al, W, or Cu, or a metal oxide such as indium tin oxide (ITO), aluminum zinc oxide (AZO), indium zinc oxide (IZO), tin oxide ($SnO_2$), or $In_2O_3$. The electron emission source 314 may be formed of a material capable of emitting electrons. For example, the electron emission source 314 may be formed of metal, silicon, an oxide, diamond, diamond like carbon (DLC), a carbide compound, a nitrogen compound, carbon nanotubes, carbon nanofibers, etc.

The cathode electrode 312 applies a voltage to the electron emission source 314. When a voltage difference occurs between the electron emission source 314 and the anode electrode 320a, that is, the cathode electrode 312 and the anode electrode 320a, the electron emission source 314 emits electrons and the electrons collide with the anode electrode 320a. Accordingly, the anode electrode 320a radiates an X-ray due to the collision of electrodes.

Figure 3B:
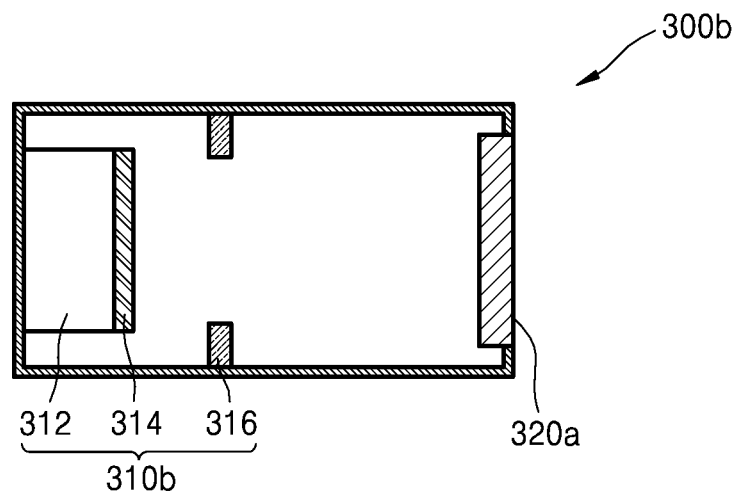

As shown in FIG. 3B, an electron emission device 310b of the X-ray generation unit 300b may further include a gate electrode 316 provided between the electron emission source 314 and the anode electrode 320a. The gate electrode 316 may be formed of the same material as the cathode electrode 312. The electron emission source 314 may emit electrons based on the voltage difference between the gate electrode 316 and the cathode electrode 312. As the gate electrode 316 is provided between the cathode electrode 312 and the anode electrode 320a, the electrons induced by the electron emission source 314 based on the voltage applied to the gate electrode 316 may be controlled. Accordingly, the X-ray generation unit 300b may more stably control the emission of electrons.

Figure 3C:
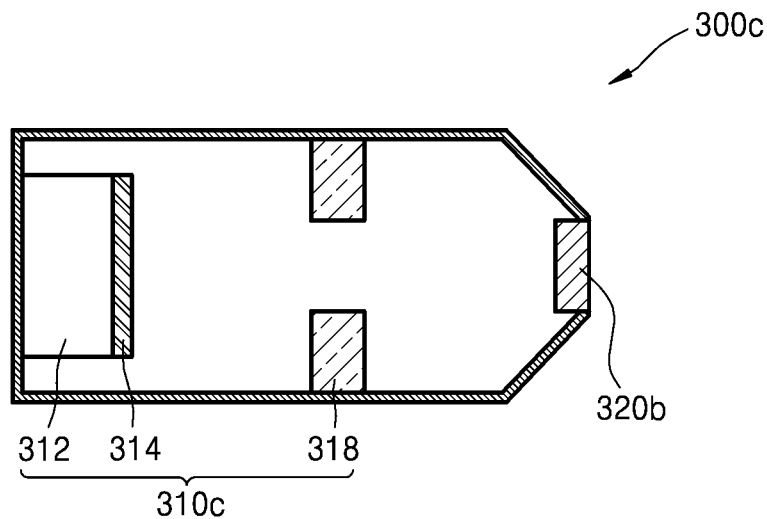

In addition, as shown in FIG. 3C, an electron emission device 310c of the X-ray generation unit 300c may further include a focusing electrode 318 provided between the electron emission source 314 and an anode electrode 320b. The focusing electrode 318 may be formed of the same material as the cathode electrode 312. The focusing electrode 318 focuses the electrons emitted from the electron emission source 314 on an area of the anode electrode 320b so as to collide the electrons therewith. A voltage applied to the focusing electrode 318 may be the same as or similar to the voltage applied to the gate electrode 316 so that an optimal focusing performance may be maintained.

Figure 3D:
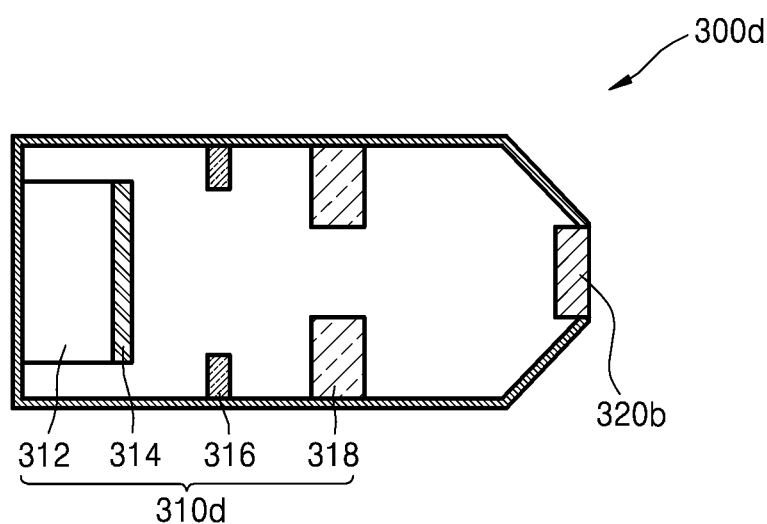

As shown in FIG. 3D, an electron emission device 310d of the X-ray generation unit 300d may include the cathode electrode 312, the electron emission source 314 that emits electrons and that is provided on the cathode electrode 312, the gate electrode 316 spaced apart from the cathode electrode 312, and the focusing electrode 318 which focuses the emitted electrons.

Figure 4:
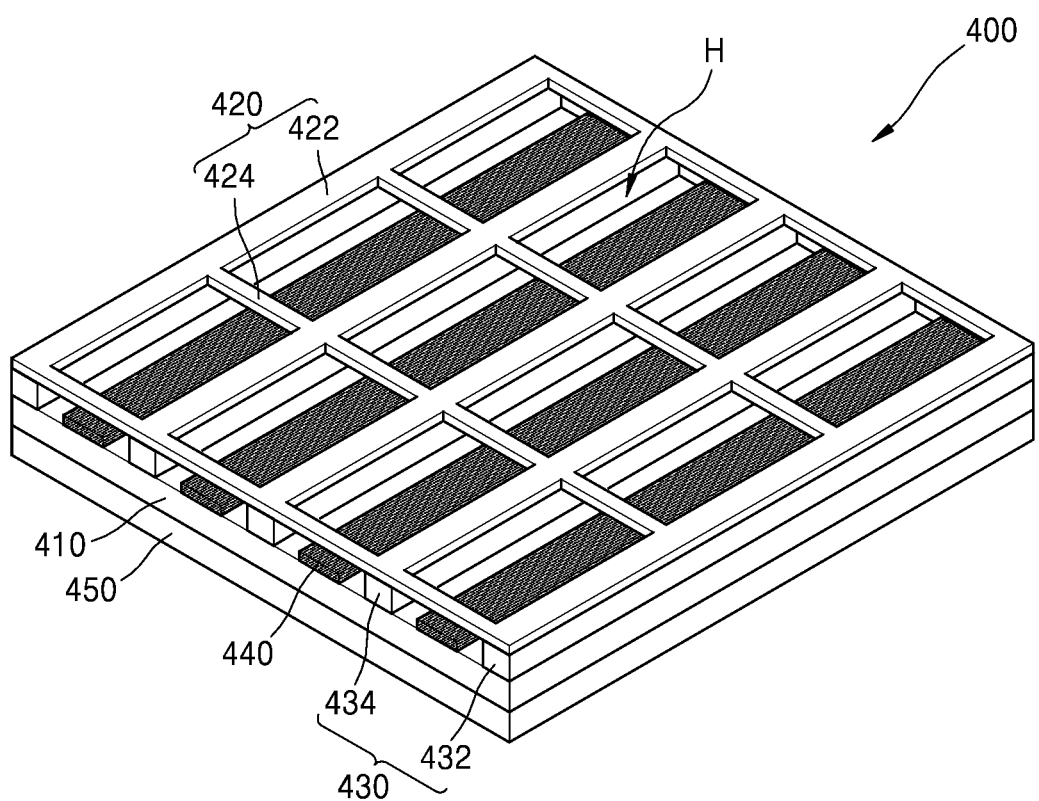
FIG. 4 illustrates an electron emission device including a gate electrode, according to an exemplary embodiment.

FIG. 4 illustrates an electron emission device 400 including a gate electrode 420, according to an exemplary embodiment.

Referring to FIG. 4, the electron emission device 400 may include a cathode electrode 410, the gate electrode 420 having a mesh structure spaced apart from the cathode electrode 410, a plurality of insulation layers 430 and a plurality of electron emission sources 440 that extend in a first direction between the cathode electrode 410 and the gate electrode 420 and are spaced apart from each other. A substrate 450 for supporting the electron emission device 400 may be formed of an insulation material such as glass. The substrate 450 may support a single electron emission device 400 or the electron emission sources 440.

The cathode electrode 410 and the gate electrode 420 may be formed of a conductive material. The cathode electrode 410 may apply a voltage to each of the electron emission sources 440 and may have a flat panel shape. When the cathode electrode 410 has a flat panel shape, the substrate 450 may not be necessary. The gate electrode 420 may have a mesh structure including a plurality of openings H. For example, the gate electrode 420 may include a plurality of gate lines 422 separated from each other and provided on the insulation layers 430, and may further include a plurality of gate bridges 424 connecting the gate lines 422. Accordingly, the two neighboring gate lines 422 and the two neighboring gate bridges 424 form the openings H.

The openings H may be provided to expose at least a part of the electron emission sources 440 between the insulation layers 430. As described above, since the gate electrode 420 has a mesh structure, a large electron emission device 400 may be manufactured. Although the openings H of the gate electrode 420 are each shown as being rectangular in FIG. 4, the exemplary embodiments are not limited thereto. Shapes of the openings H may be various other types of shapes, such as at least one of circles, ovals, and polygons. The sizes of the openings H may be identical or different from each other.

The insulation layers 430 are provided between the cathode electrode 410 and the gate electrode 420 and prevent electrical connection between the cathode electrode 410 and the gate electrode 420. The insulation layers 430 are provided in multiple numbers and at least three insulation layers 430 may be provided. The insulation layers 430 may have a linear shape. The insulation layers 430 extend in one direction and are separate from one another and support the gate electrode 420. The insulation layers 430 may each include a first insulation layer 432 supporting an edge area of the gate electrode 420 and a second insulation layer 434 supporting a middle area of the gate electrode 420.

The insulation layers 430 may be formed of an insulation material used for a semiconductor device. For example, the insulation layers 430 may be formed of HfO2, Al2O3, or Si3N4, which is a high-K material having a higher dielectric rate than SiO2 or SiO2, or a mixture thereof.

Although the insulation layers 430 are shown as having a linear shape in FIG. 4, the exemplary embodiments are not limited thereto. The insulation layers 430 may have a different shape that prevents an electrical connection between the cathode electrode 410 and the gate electrode 420 and supports the gate electrode 420. For example, the second insulation layer 434 may have a column shape and may be provided under the gate lines 422.

The electron emission sources 440 emit electrons due to the voltage applied to the cathode electrode 410 and the gate electrode 420. The electron emission device 400 of FIG. 4 may include the electron emission sources 440. The electron emission sources 440 may be alternately provided with the insulation layers 430. For example, the electron emission sources 440 may be spaced apart from one another with the second insulation layer 434 interposed between the neighboring electron emission sources 440. The electron emission sources 440 may be shaped as strips extending in the first direction, similar to the second insulation layer 434.

Since the gate electrode 420 has a mesh structure, the gate electrode 420 is provided above the electron emission sources 440. The electron emission sources 440 may be spaced apart from the gate electrode 420 to prevent the electron emission sources 440 and the gate electrode 420 from being short-circuited.

The electron emission sources 440 may be formed of a material capable of emitting electrons. As an area occupied by the electron emission sources 440 in the electron emission device 400 increases, the electron emission device 400 may emit a large amount of electrons. However, the electron emission device 400 may endure an electrostatic force due to a difference in the voltages applied between the electron emission sources 440 and the gate electrode 420. Accordingly, the insulation layers 430 and the electron emission sources 440 are alternately provided, and the gate electrode 420 having the openings H is provided over an area where each of the electron emission sources 440 is provided, thereby implementing the large area electron emission device 400.

Since the gate electrode 420 includes the gate bridges 424 provided in a direction crossing the lengthwise direction of the electron emission sources 440, a uniform electric field may be formed on surfaces of the electron emission sources 440.

Although the electron emission sources 440 are shown as being formed in strips in FIG. 4, the exemplary embodiments are not limited thereto. The electron emission sources 440 may be formed as a point type in an area corresponding to the openings H above the cathode electrode 410. The point-type electron emission sources 440 may be provided in a two dimensional array, that is, in a matrix format.

Although the electron emission sources 440 are shown as being provided in the single electron emission device 400 in FIG. 4, the exemplary embodiments are not limited thereto. Also, only one electron emission source may be provided in the electron emission device 400 or two or more electron emission sources may be provided therein.

A proceeding path of the X-ray may be controlled by the shape of an anode electrode. In detail, as the thickness of the anode electrode is provided to be irregular, the proceeding path of the X-ray radiated from the anode electrode may be controlled.

FIGS. 5A to 5G illustrate anode electrodes having irregular thicknesses according to exemplary embodiments. The anode electrode illustrated in each of FIGS. 5A to 5G corresponds to a single X-ray generator. However, the exemplary embodiments are not limited thereto. One anode electrode may correspond to one electron emission device. For convenience of explanation, one anode electrode corresponding to a single X-ray generator will be described below.

As shown in FIGS. 5A to 5G, the anode electrode may be symmetrically provided about a center axis X of the X-ray generator 10 so that an X-ray may be symmetrically radiated.

Figure 5A:
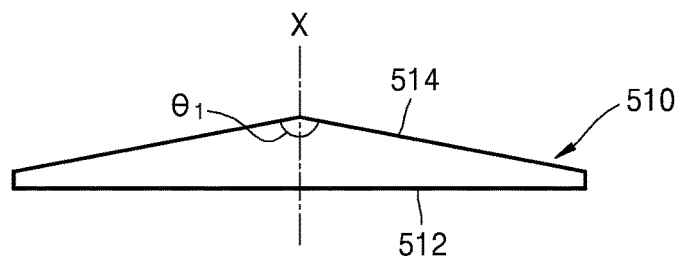
FIGS. 5A to 5G illustrate anode electrodes having irregular thicknesses, according to exemplary embodiments.
Figure 5B:
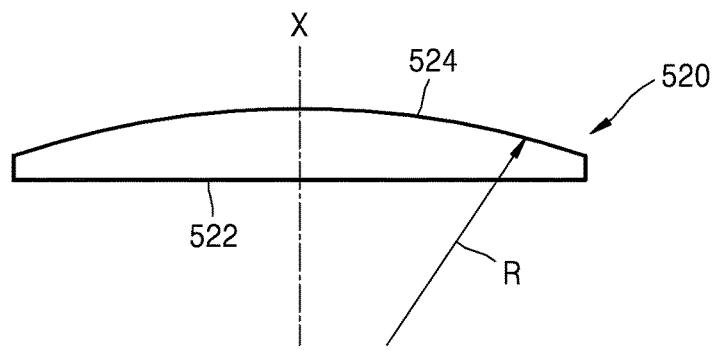

The thicknesses of anode electrodes 510 and 520 gradually decrease from the center axis X of the X-ray generator 10 toward edges thereof, as illustrated in FIGS. 5A and 5B. When the thicknesses of the anode electrodes 510 and 520 gradually decrease from the center axis X of the X-ray generator 10 toward edges thereof, X-rays radiated from the anode electrodes 510 and 520 may propagate to be focused at the center axis X of the X-ray generator 10. Thus, the X-ray generator 10 may efficiently radiate an X-ray in a partial area of the object.

In more detail, surfaces 512 and 522 of the anode electrodes 510 and 520, on which electrons are incident, may be flat surfaces, whereas surfaces 514 and 524 from which X-rays are emitted may be convex surfaces. The surfaces 514 and 524 from which X-rays are emitted may be convexly curved surfaces or convex surfaces obtained by combining flat surfaces. A position where the X-ray is focused may be determined by levels, θ and R, of the convex shape. Although FIGS. 5A and 5B illustrate that the surfaces 512 and 522 of the anode electrodes 510 and 520 on which electrons are incident are flat and the surfaces 514 and 524 from which X-rays are emitted are convex, the exemplary embodiments are not limited thereto. That is, the surfaces on which electrons are incident may be convex, whereas the surfaces from which X-rays are emitted may be flat.

Figure 5C:
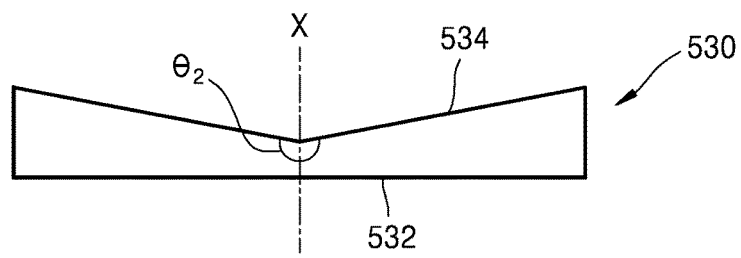
Figure 5D:
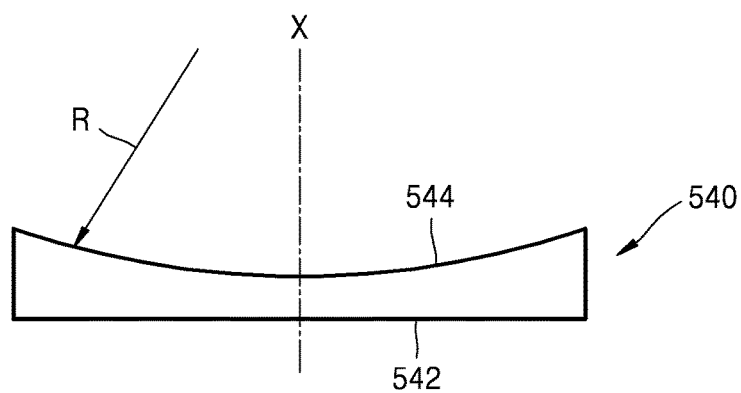

The thicknesses of anode electrodes 530 and 540 gradually increase from the center axis X of the X-ray generator 10 toward edges thereof, as illustrated in FIGS. 5C and 5D. When the thicknesses of the anode electrodes 530 and 540 increase from the center axis X of the X-ray generator 10 toward edges thereof, the X-rays radiated from each of the anode electrodes 530 and 540 may propagate toward an area larger than a sectional area of each of the anode electrodes 530 and 540. Thus, the X-ray generator 10 may radiate an X-ray to a relatively large area of an object.

In more detail, surfaces 532 and 542 of the anode electrode 530 and 540, on which electrons are incident, may be flat surfaces, whereas surfaces 534 and 544 from which X-rays are emitted may be concave surfaces. The surfaces 534 and 544 from which X-rays are emitted may be concavely curved surfaces or concave surfaces obtained by combining flat surfaces. A size of an area where the X-ray is radiated may be determined by levels, θ and R, of the concave shape. Although FIGS. 5C and 5D illustrate that the surfaces 532 and 542 of the anode electrodes 530 and 540 on which electrons are incident are flat and the surfaces 534 and 544 from which X-rays are emitted are concave, the exemplary embodiments are not limited thereto. That is, the surfaces on which electrons are incident may be concave, whereas the surfaces from which X-rays are emitted may be flat.

Figure 5E:
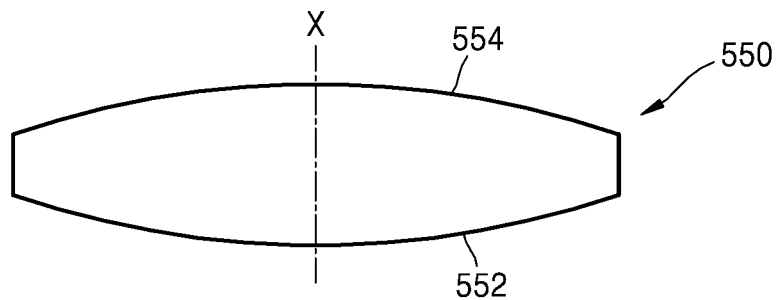

In addition, as shown in FIG. 5E, both surfaces of an anode electrode 550, including a surface on which electrons are incident and a surface from which X-rays are emitted, may be convex. In this case, a focal distance of an X-ray may become shorter. Additionally, both surfaces on which electrons are incident and from which X-rays are emitted may be concave. Alternatively, while one of the surfaces on which electrons are incident and from which X-rays are emitted may be concave, the other surface may be convex.

Figure 5F:
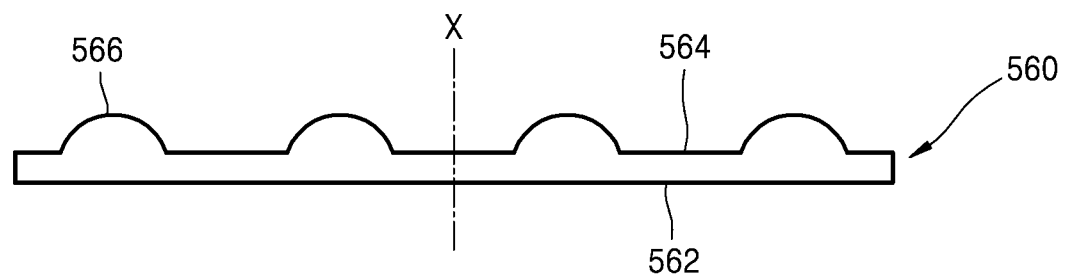
Figure 5G:
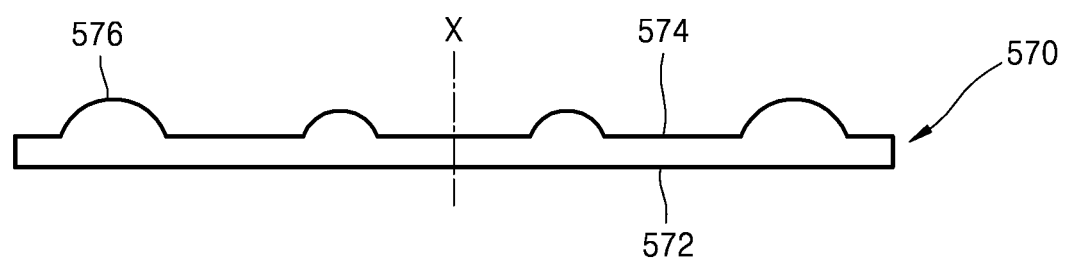

The thickness of an anode electrode may be partially irregular. For example, as illustrated in FIGS. 5F and 5G, anode electrodes 560 and 570 may have a shape in which only some parts are convex. A convex shape 566 may be identical to others or a convex shape 576 may be different from others according to an area. Nevertheless, the thicknesses of the anode electrodes 560 and 570 may be symmetrical with respect to the center axis Z of the X-ray generator 10. Although FIGS. 5F and 5G illustrate only a convex shape, the exemplary embodiments are not limited thereto. The anode electrode may have a concave shape or both a concave shape and a convex shape.

As such, since the propagating path of an X-ray may be controlled by using the anode electrode having an irregular thickness, the X-ray generator 10 may not only efficiently radiate an X-ray to the object but may also reduce an unnecessary X-ray radiation dose.

Figure 6:
FIG. 6 illustrates an anode electrode having a uniform thickness, according to an exemplary embodiment.

The X-ray photographing apparatus 100 according to an exemplary embodiment may use an anode electrode having a uniform thickness. FIG. 6 illustrates an anode electrode 580 having a uniform thickness, according to an exemplary embodiment. Referring to FIG. 6, while the anode electrode 580 having a uniform thickness is used, the propagating path of an X-ray may be controlled by using a separate constituent element such as a collimator (not shown).

Figure 7:
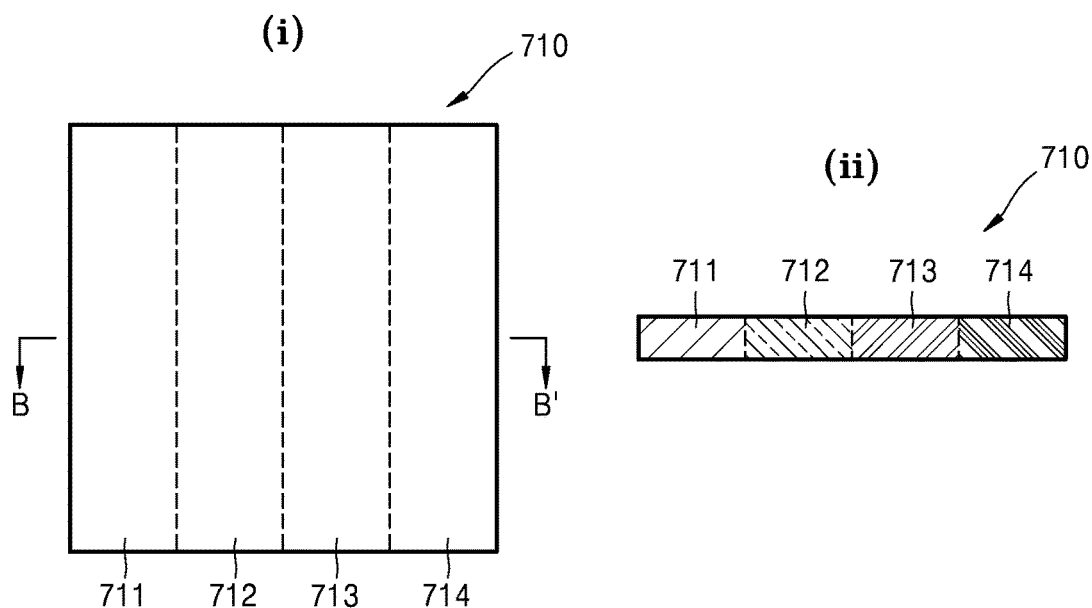
FIG. 7 illustrates an anode electrode formed of different materials, according to an exemplary embodiment.

In addition, the anode electrode may include a plurality of layers formed of different materials and capable of radiating X-rays of different wavelengths. FIG. 7 illustrates an anode electrode 710 formed of different materials, according to an exemplary embodiment. As shown in FIG. 7, the anode electrode 710 may include a plurality of layers 711, 712, 713, and 714 formed of different materials. The layers 711, 712, 713, and 714 may be provided in a parallel fashion with respect to an electron emission device. The anode electrode 710 may radiate X-rays of different wavelengths according to the layers 711, 712, 713, and 714 with which electrons collide.

Figure 8A:
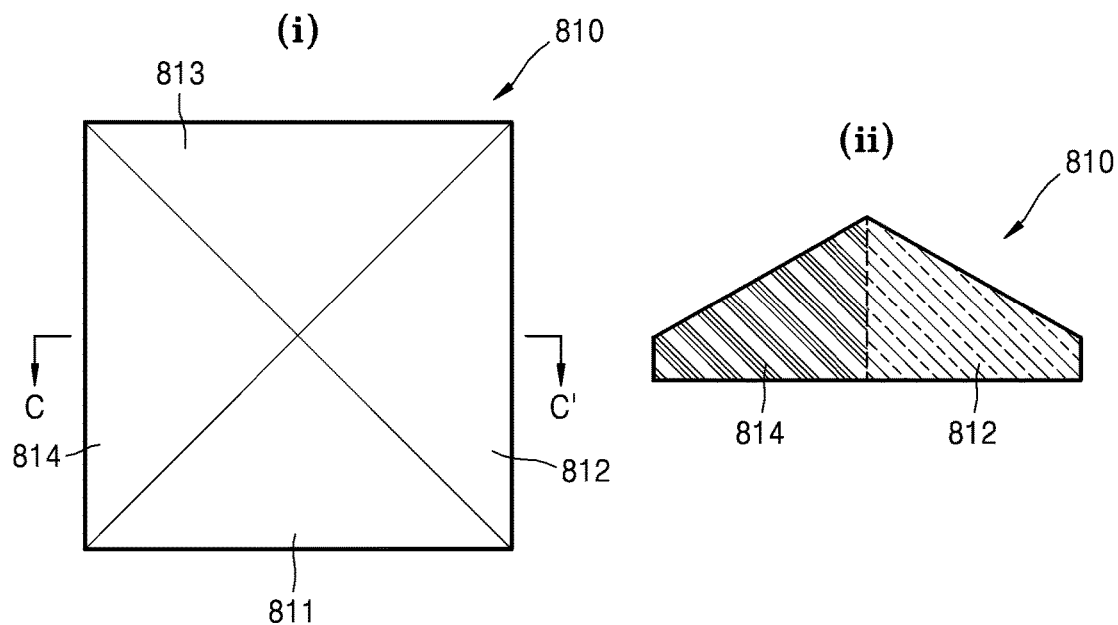
FIGS. 8A and 8B illustrate anode electrodes formed of different materials, according to exemplary embodiments.
Figure 8B:
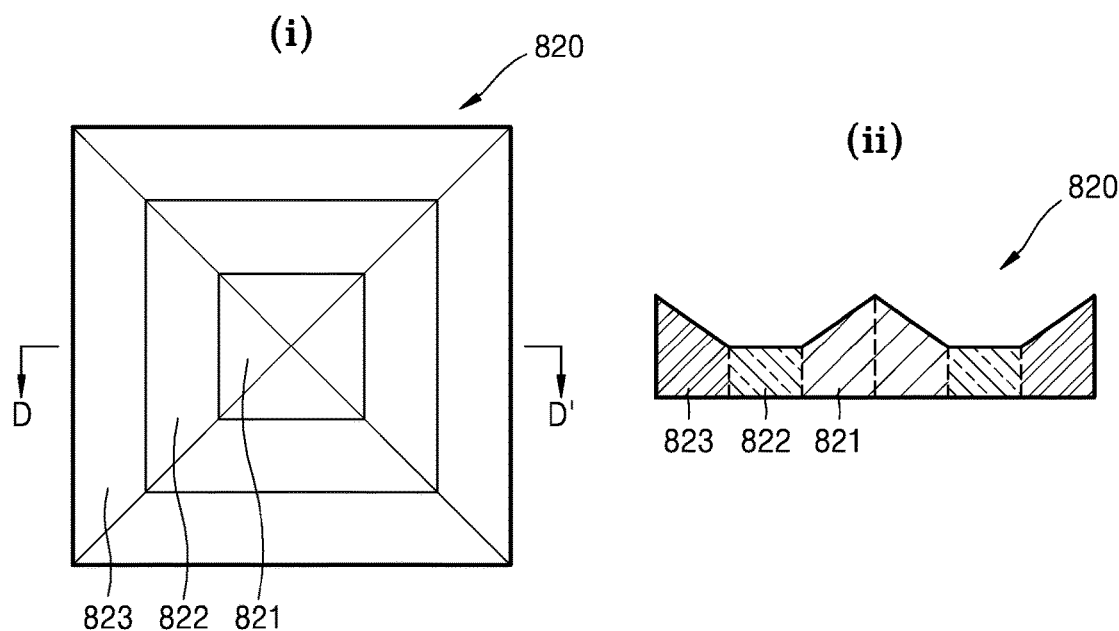

An anode electrode radiating X-rays of multiple wavelengths may not have a uniform thickness as described above. FIGS. 8A and 8B illustrate anode electrodes 810 and 820 formed of different materials, according to exemplary embodiments. Each of the anode electrodes 810 and 820 may include a plurality of layers formed of different materials and at least one of the layers may have an irregular thickness.

For example, as shown in FIG. 8A, the anode electrode 810 may include a plurality of layers 811, 812, 813, and 814 that are formed of different materials. The layers 811, 812, 813, and 814 have thicknesses that gradually decrease from the center axis X of the X-ray generator 10 toward edges thereof. Accordingly, the anode electrode 810 may focus the radiated X-rays. Since the X-rays having different wavelengths are focused on different areas, a single linear X-ray generator may photograph many different areas at different depths of the object at one time.

In addition, as shown in FIG. 8B, the anode electrode 820 may include a plurality of layers 821, 822, and 823 that are formed of different materials. The anode electrode 820 may have a change in the thickness thereof according to the layers 821, 822, and 823. For example, the first layer 821 may have a thickness that gradually decreases from the center axis X of the X-ray generator 10 toward an edge thereof, the second layer 822 may have a uniform thickness, and the third layer 823 may have a thickness that gradually increases from the center axis X of the X-ray generator 10 toward the edge thereof. Accordingly, the anode electrode 820 may radiate an X-ray to a larger surrounding area while focusing on an area of interest of the object.

Figure 9A:
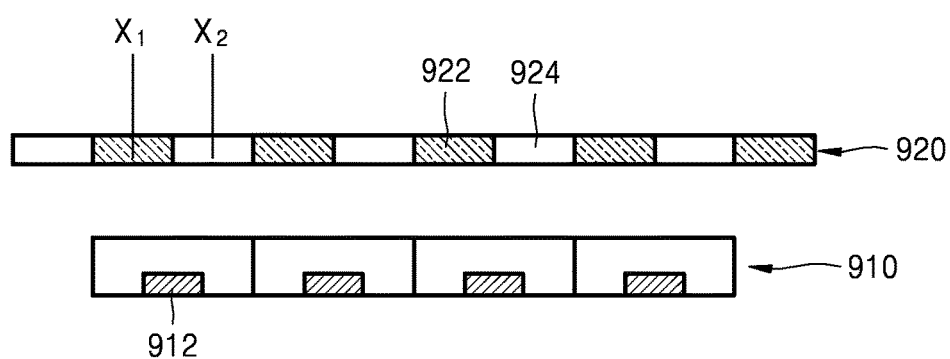
FIGS. 9A to 9C illustrate an X-ray generator generating an X-ray of a short wavelength or an X-ray of a plurality of wavelength bands according to exemplary embodiments.
Figure 9B:
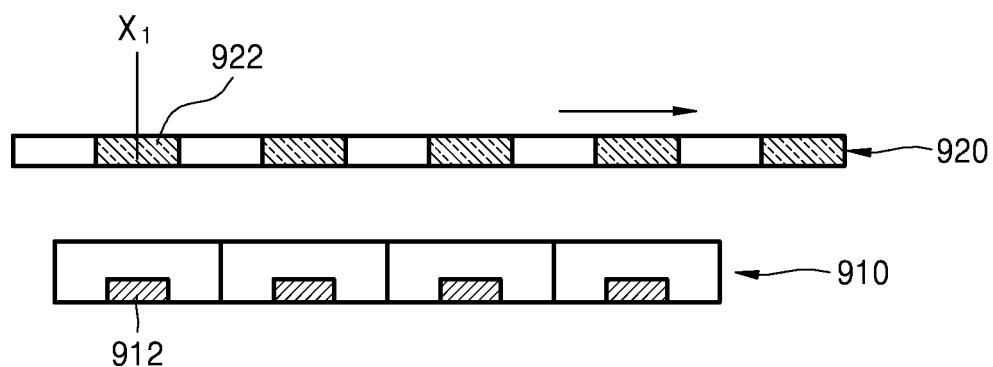
Figure 9C:
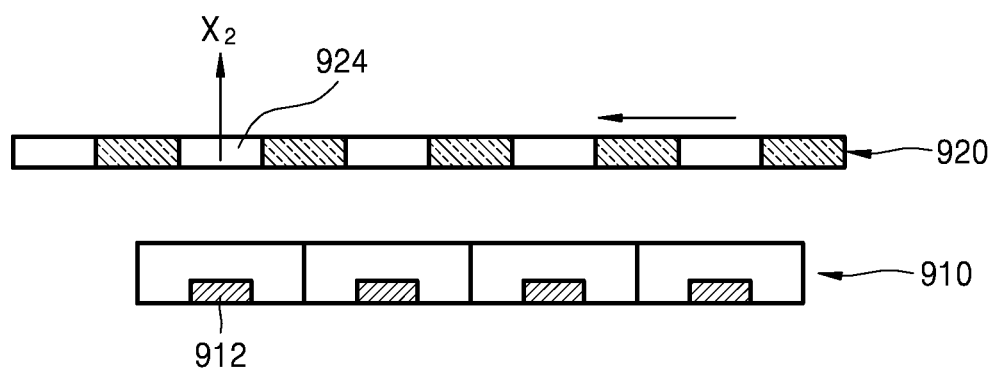

The X-ray generator 10 according to the present exemplary embodiment may simultaneously or selectively generate X-rays of different wavelengths. FIGS. 9A to 9C illustrate an X-ray generator generating an X-ray of a short wavelength or simultaneously generating X-rays of a plurality of wavelength bands, according to exemplary embodiments.

Referring to FIG. 9A, a plurality of electron emission devices 910, each having an electron emission source 912, are provided and an anode electrode 920 may be provided separately from the electron emission devices 910. In the anode electrode 920, first and second layers 922 and 924 that are formed of different materials may be alternately provided. When the first and second layers 922 and 924 overlap with each other in an area corresponding to the electron emission source 912 of one of the electron emission devices 910, electrons emitted by the electron emission devices 910 may collide with the first and second layers 922 and 924. Accordingly, the anode electrode 920 may simultaneously radiate a first X-ray X1 and a second X-ray X2.

As shown in FIG. 9B, the anode electrode 920 makes a translational movement in parallel with the electron emission devices 910 such that the first layer 922 of the anode electrode 920 may be arranged to overlap with the electron emission source 912. Then, the electrons emitted by the electron emission devices 910 collide with the first layer 922, and thus, the first X-ray X1 may be radiated from the anode electrode 920.

As shown in FIG. 9C, the anode electrode 920 makes a translational movement in parallel with the electron emission devices 910 such that the second layer 924 of the anode electrode 920 may be arranged to overlap with the electron emission source 912. Then, the electrons emitted by the electron emission devices 910 collide with the second layer 924, and thus the second X-ray X2 may be radiated from the anode electrode 920.

As such, since the anode electrode 920 simultaneously radiates a plurality of X-rays or selectively radiates a single X-ray, usability of the X-ray generator 10 may be improved.

As described above, X-ray generation units are provided in an X-ray generator 10. Each of the X-ray generation units is separately manufactured as one unit and then the X-ray generation units are assembled, thereby forming the X-ray generator 10. A plurality of electron emission devices and an anode electrode may be integrally manufactured on a single substrate. Alternatively, a plurality of electron emission devices may be manufactured on a single substrate and then an anode electrode may be assembled, thereby forming a linear X-ray generator. In addition, the linear X-ray generator may be formed by a variety of different methods.

Additionally, the X-ray generator may further include a collimator (not shown) for controlling a proceeding direction of an X-ray. Accordingly, an unnecessary X-ray radiation dose may be reduced, and an X-ray may be also more accurately detected.

Figure 10A:
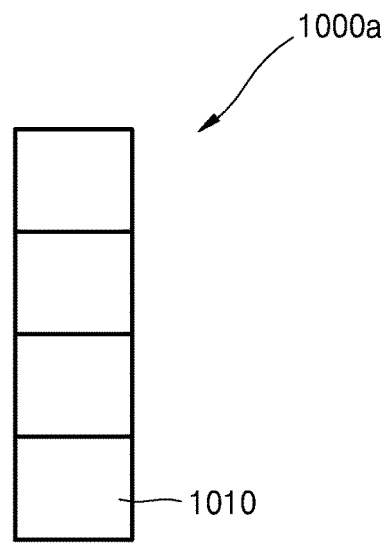
FIGS. 10A and 10B schematically illustrate X-ray detectors that may be applied to the X-ray detector of FIG. 1.
Figure 10B:
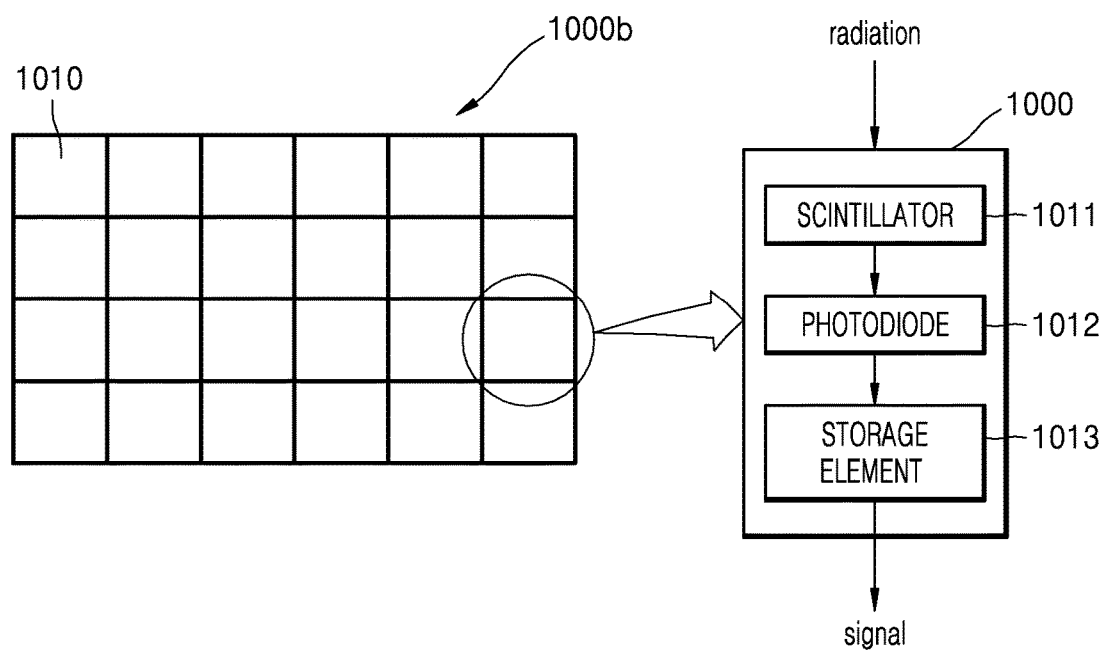

FIGS. 10A and 10B schematically illustrate X-ray detectors 1000a and 1000b that may be used as the X-ray detector 20 of FIG. 1. As shown in FIG. 10A, the X-ray detector 1000a may be configured as a plurality of X-ray detection units 1010 provided in one dimension. Alternatively, as shown in FIG. 10B, the X-ray detector 1000b may be configured as the plurality of X-ray detection units 1010 provided in two dimensions.

Each of the X-ray detection units 1010 is a light-receiving element that receives an X-ray and converts a received X-ray into an electric signal, and may include, for example, a scintillator 1011, a photodiode 1012, and a storage element 1013. The scintillator 1011 receives an X-ray and outputs photons, in particular visible photons, that is, a visible ray, according to a received X-ray. The photodiode 1012 receives the photons output from the scintillator 1011 and converts the received photons into electric signals. The storage element 1013 is electrically connected to the photodiode 1012 and stores the electric signal output from the photodiode 1012. In this regard, the storage element 1013 may be, for example, a storage capacitor. The electric signal stored in the storage element 1013 of each of the X-ray detection units 1010 is transmitted to a processor (not shown) where the signal is processed into an X-ray image.

The X-ray detectors 1000a and 1000b may detect an X-ray by using a photoconductor configured to directly convert an X-ray into an electric signal.

The X-ray detection units 1010 may be provided to correspond to the X-ray generation units 300 of an X-ray generator. The X-ray generation units 300 and the X-ray detection units 1010 may have a one-to-one correspondence. Alternatively, each of the X-ray generation units 300 may correspond to two or more X-ray detection units 1010, or two or more X-ray generation units 300 may correspond to one X-ray detection unit 1010.

The X-ray detection units 1010 may be simultaneously or independently driven to detect an X-ray. Accordingly, an X-ray passing through the entire area of the object may be detected as all of the X-ray detection units 1010 are driven, or an X-ray passing through a particular area of the object may be detected as some of the X-ray detection units 1010 are driven. Also, at least one of the X-ray detection units 1010 may be simultaneously or sequentially driven.

Although the X-ray detection units 1010 are shown as being formed on a single substrate, the exemplary embodiments are not limited thereto. Each of the X-ray detection units 1010 may be separately manufactured, and the X-ray detection units 1010 may be assembled into the X-ray detectors 1000*a* and 1000*b*. Alternatively, some of the X-ray detection units 1010 may be formed on a single substrate and then assembled together with the other X-ray detection units 1010 formed on other substrates. For example, X-ray detectors in one dimension may be provided on a single substrate and then arranged, and thus, X-ray detectors in two dimensions may be manufactured.

When an X-ray generation area of the X-ray generator and X-ray detection areas of the X-ray detectors 1000*a* and 1000*b* are equal to or larger than a test area of the object, the linear X-ray generator and the X-ray detectors 1000*a* and 1000*b* may photograph the object by performing one operation. The X-ray photographing apparatus 100 may photograph the whole object at one time or a partial area of the object. When a partial area of the object is to be photographed, only some of the X-ray generation units 300 of the X-ray generator may operate to generate an X-ray, and only some of the X-ray detection units 1010 corresponding to the operating X-ray generation units 300 may be synchronized to detect the X-ray.

However, when at least one of the X-ray generation area of the X-ray generator and the X-ray detection areas of the X-ray detectors 1000*a* and 1000*b* is smaller than the test area of the object, at least one of the X-ray generator and the X-ray detectors 1000*a* and 1000*b* may be moved and driven two times or more.

Figure 11A:
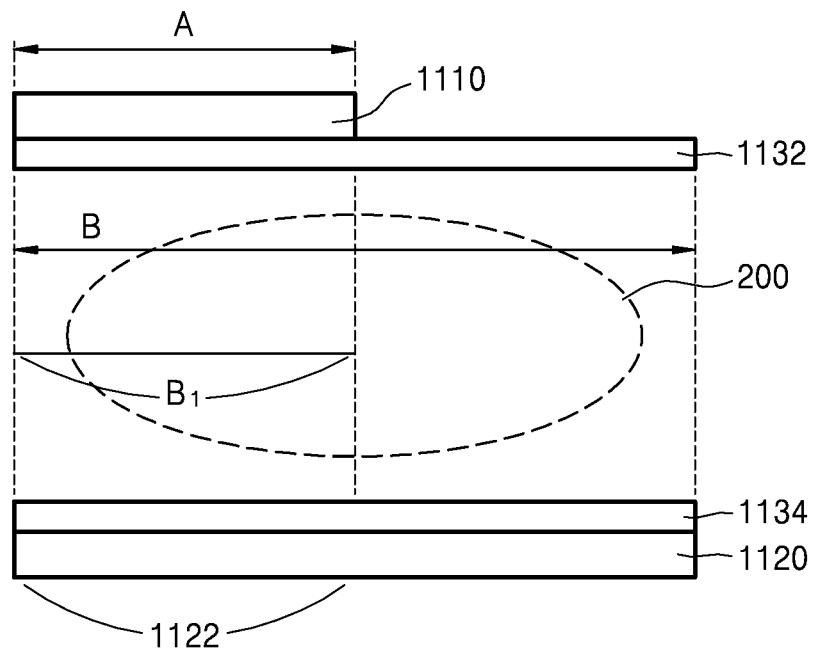
FIGS. 11A and 11B are diagrams for explaining an X-ray photographing method when an X-ray generation area is smaller than a test area of an object according to an exemplary embodiment.
Figure 11B:
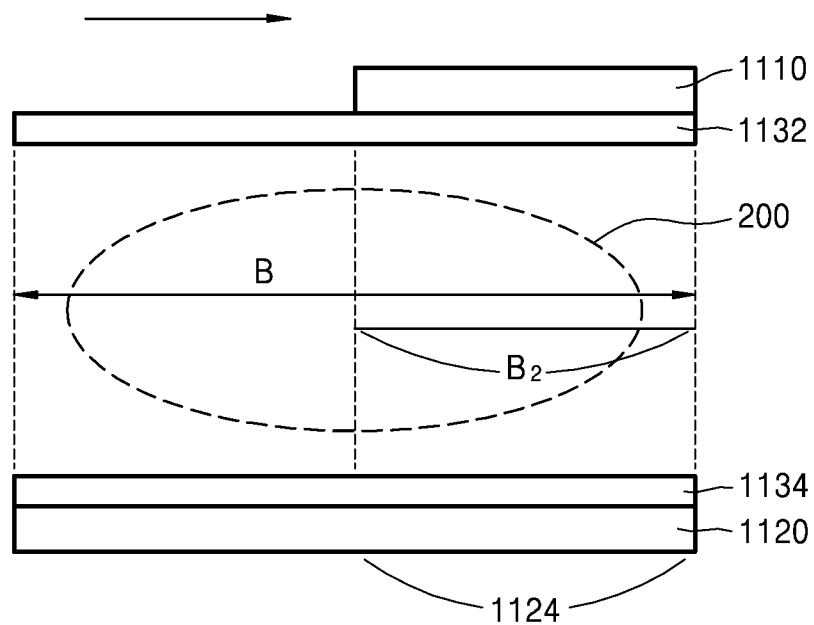

FIGS. 11A and 11B are diagrams for explaining an X-ray photographing method when an X-ray generation area A is smaller than a test area B of the object 200 according to an exemplary embodiment. When the X-ray generation area A of an X-ray generator 1110 is smaller than the test area B, the X-ray generator 1110 may move along a first panel 1132 to generate an X-ray, thereby generating the X-ray in the entire test area B of the object 200.

For example, referring to FIG. 11A, the X-ray generator 1110 radiates an X-ray to a first area B1 of the object 200. Then, a first detector 1122 of an X-ray detector 1120 detects an X-ray that was transmitted to the first area B1. Referring to FIG. 11B, the X-ray generator 1110 horizontally moves along the first panel 1132 and then radiates an X-ray to a second area B2 of the object 200. In this regard, the second area B2 and the first area B1 may not overlap with each other. Thus, an X-ray radiation dose of the object 200 may be minimized. A second detector 1124 of the X-ray detector 1120 corresponding to the second area B2 detects an X-ray of the second area B2. Although the X-ray generation area A of the X-ray generator 1110 is ½ the test area B in FIGS. 11A and 11B, the exemplary embodiments are not limited thereto. The X-ray generation area A may be 1/n (where n is a natural number equal to or greater than 2) the test area B.

Figure 12A:
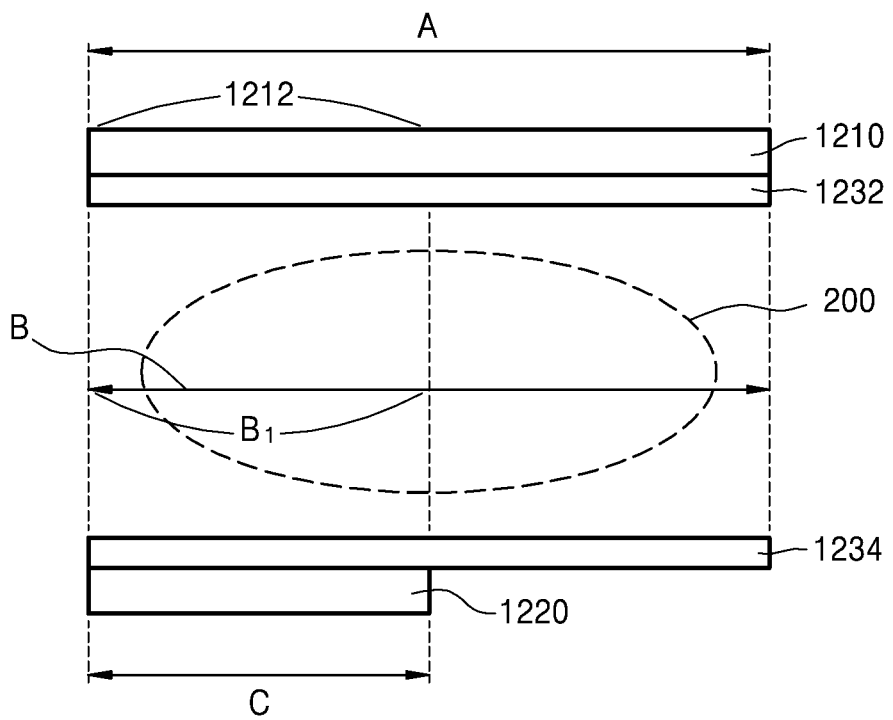
FIGS. 12A and 12B are diagrams for explaining an X-ray photographing method when an X-ray detection area is smaller than a test area of an object according to an exemplary embodiment.
Figure 12B:
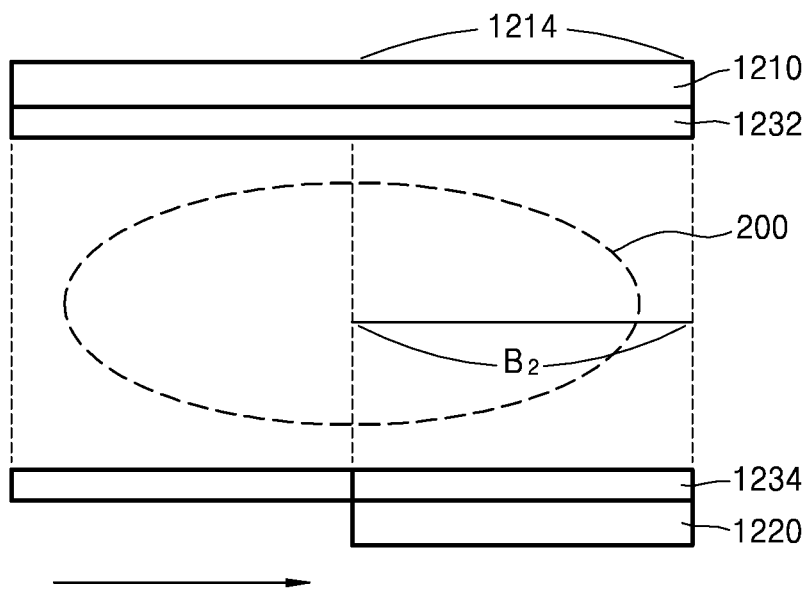

FIGS. 12A and 12B are diagrams for explaining an X-ray photographing method when an X-ray detection area C is smaller than the test area B of an object according to an exemplary embodiment. When the X-ray detection area C of the X-ray detector 1120 is smaller than the test area B, the X-ray detector 1120 may move along a second panel 1234 to detect an X-ray, thereby detecting the X-ray that is transmitted to the entire test area B of the object 200.

For example, referring to FIG. 12A, a first X-ray generator 1212 of an X-ray generator 1210 generates X-rays to be transmitted to the first area B1 of the object 200. Then, an X-ray detector 1220 detects an X-ray of the first area B1. Referring to FIG. 12B, the X-ray detector 1220 horizontally moves along the second panel 1234. Then, a second X-ray generator 1214 of the X-ray generator 1210 generates X-rays to be transmitted to the second area B2 of the object 200. The X-ray detector 1220 detects an X-ray of the second area B2. In this regard, the second area B2 and the first area B1 may not overlap with each other. Thus, an X-ray radiation dose of the object 200 may be minimized. Although the X-ray detection area C of the X-ray detector 1120 is ½ the test area B in FIGS. 12A and 12B, the exemplary embodiments are not limited thereto. The X-ray detection area C may be 1/n (where n is a natural number equal to or greater than 2) the test area B.

In addition, when the X-ray generation area A and the X-ray detection area C are smaller than the test area B and correspond to each other one-to-one, the X-ray generators 1110 and 1210 and the X-ray detectors 1120 and 1220 may be synchronized to photograph a partial region of the test area B. Each of the X-ray generators 1110 and 1210 and the X-ray detectors 1120 and 1220 may horizontally move along the first and second panels 1132 and 1234 and photograph other regions of the test area B.

When the X-ray generation area A and the X-ray detection area C are smaller than the test area B, and the X-ray generation area A is smaller than the X-ray detection area C, the X-ray photographing method of FIGS. 12A and 12B may be applied to photograph a partial region of the test area B. Each of the X-ray generators 1110 and 1210 and the X-ray detectors 1120 and 1220 may horizontally move along the first and second panels 1132 and 1234 and photograph other regions of the test area B. Furthermore, when the X-ray generation area A and the X-ray detection area C are smaller than the test area B, and the X-ray detection area C is smaller than the X-ray generation area A, the X-ray photographing method of FIGS. 12A and 12B may be applied to photograph a partial region of the test area B. Each of the X-ray generators 1110 and 1210 and the X-ray detectors 1120 and 1220 may horizontally move along the first and second panels 1132 and 1234 and photograph other regions of the test area B.

The X-ray photographing apparatus 100 according to an exemplary embodiment may acquire a tomography image of the object 200. To acquire the tomography image, the X-ray generators may radiate an X-ray to the object by varying a radiation angle to the object. The X-ray generators according to an exemplary embodiment may vary the radiation angle to the object by horizontally moving with respect to the object. In this regard, horizontal moving refers to horizontal moving of center axes of the X-ray generators.

To acquire the tomography image, the X-ray generators may radiate an X-ray to the object at multiple locations. When the X-ray is radiated at multiple locations, the center axes of the X-ray generators may move in parallel to the object. Furthermore, the X-ray generators may radiate an X-ray by varying a radiation angle according to locations thereof. For example, the X-ray generators may radiate an X-ray to the object vertically at a first location and in an inclined fashion at a second location. In this regard, the X-ray detectors may be disposed under the object. The X-ray detectors may be fixed, although are not limited thereto.

Figure 13A:
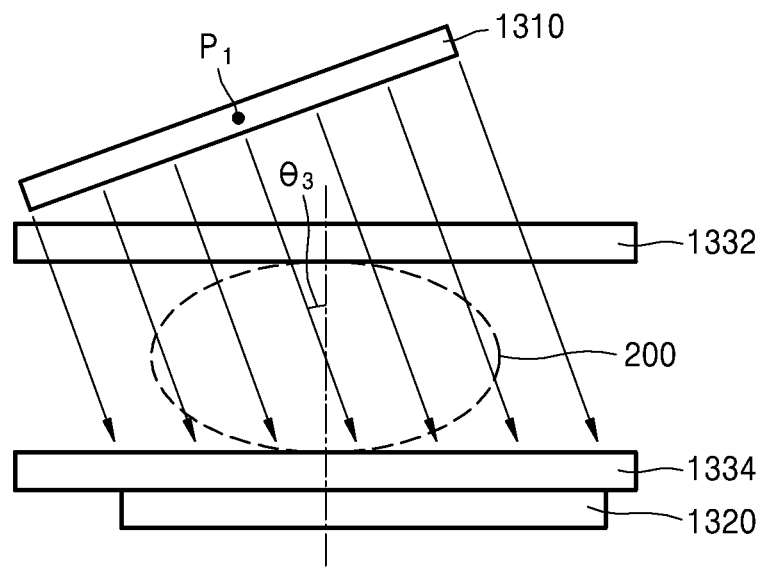
FIGS. 13A through 13C are diagrams for explaining an X-ray photographing method which may be used to acquire a tomography image according to an exemplary embodiment.
Figure 13B:
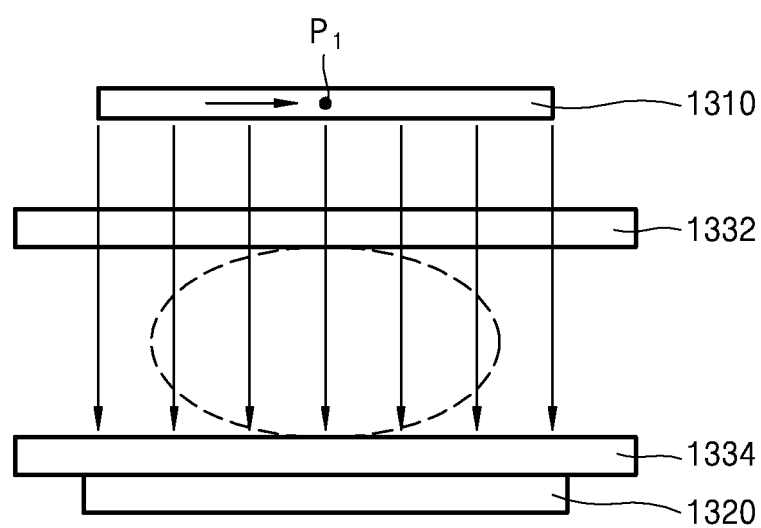
Figure 13C:
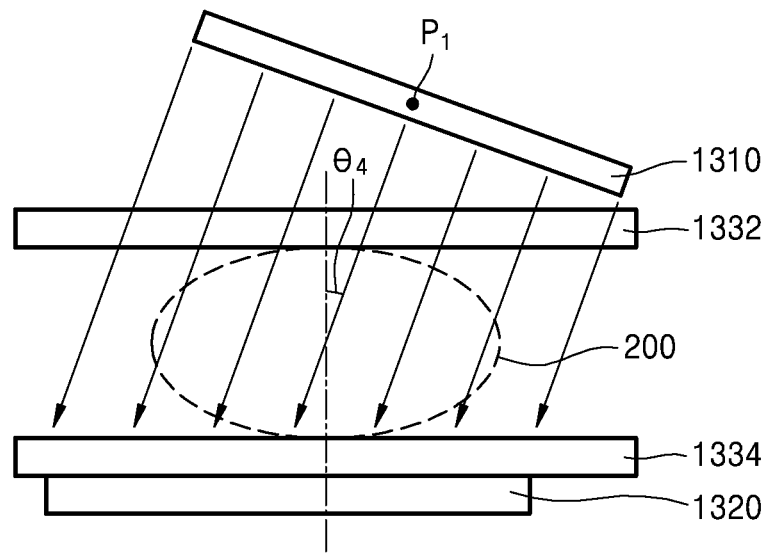

FIGS. 13A through 13C are diagrams for explaining an X-ray photographing method which may be used to acquire a tomography image according to an exemplary embodiment. Referring to FIG. 13A, when an X-ray generator 1310 is disposed on a left upper portion of the object 200, the X-ray generator 1310 may rotate with respect to a center axis P1 thereof such that an X-ray radiation direction is changed from the left upper portion to a right lower portion. The X-ray generator 1310 radiates an X-ray at a first radiation angle θ3 toward the object 200, and thus, an X-ray photographing apparatus may photograph a first image of the object 200.

The X-ray generator 1310 may move to the right. When the X-ray generator 1310 moves, the center axis P1 of the X-ray generator 1310 may move in parallel to the object 200. When the X-ray generator 1310 is disposed on the object 200, the X-ray generator 1310 may adjust its posture to allow an X-ray to face the object 200. For example, the X-ray generator 1310 may rotate in a clockwise direction with respect to the center axis P1 of the X-ray generator 1310, and thus, as shown in FIG. 13B, the X-ray generator 1310 may be disposed in parallel to the object 200. The X-ray generator 1310 may vertically radiate an X-ray to the object 200. The X-ray photographing apparatus may photograph a second image of the object 200.

The X-ray generator 1310 may move in parallel to the right until the X-ray generator 1310 is disposed on a right upper portion of the object 200. When the X-ray generator 1310 is disposed on the right upper portion of the object 200, the X-ray generator 1310 may adjust its posture to allow an X-ray generated by the X-ray generator 1310 to be radiated in an inclined fashion to the object 200. For example, as shown in FIG. 13C, the X-ray generator 1310 may rotate in a clockwise direction with respect to the center axis P1 of the X-ray generator 1310. The X-ray generator 1310 may radiate an X-ray at a second radiation angle θ4 toward the object 200, and thus, the X-ray photographing apparatus may photograph a third image of the object 200.

When the X-ray generator 1310 moves in a horizontal direction with respect to an X-ray detector 1320, the X-ray generator 1310 rotates with respect to the center axis P1 thereof according to a location. An order of horizontal movement and rotational movement may be switched, and the second image of the object 200 may be photographed in advance and the first image or the third image may be photographed.

Figure 14A:
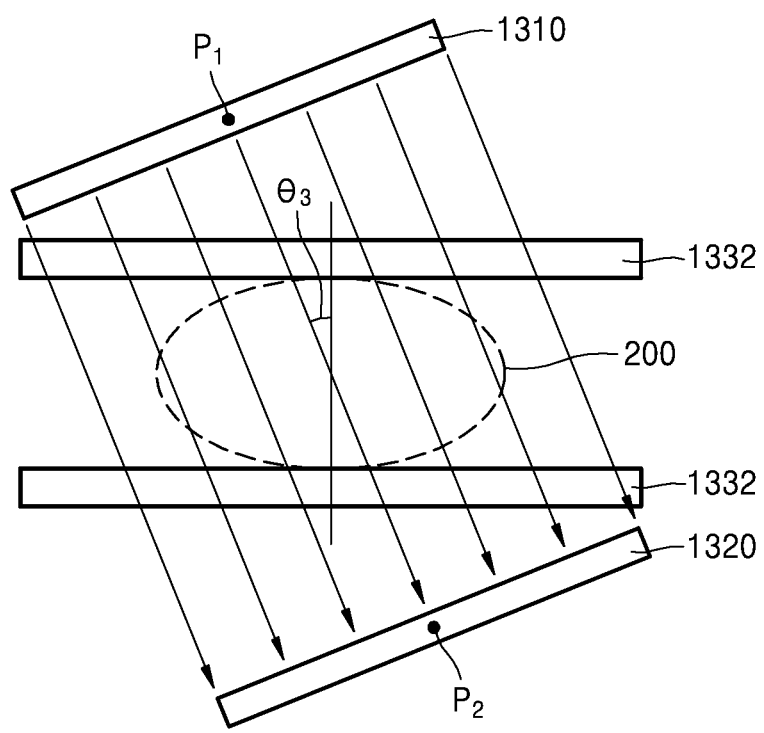
FIGS. 14A through 14C are diagrams for explaining an X-ray photographing method which may be used to acquire a tomography image according to another exemplary embodiment.
Figure 14B:
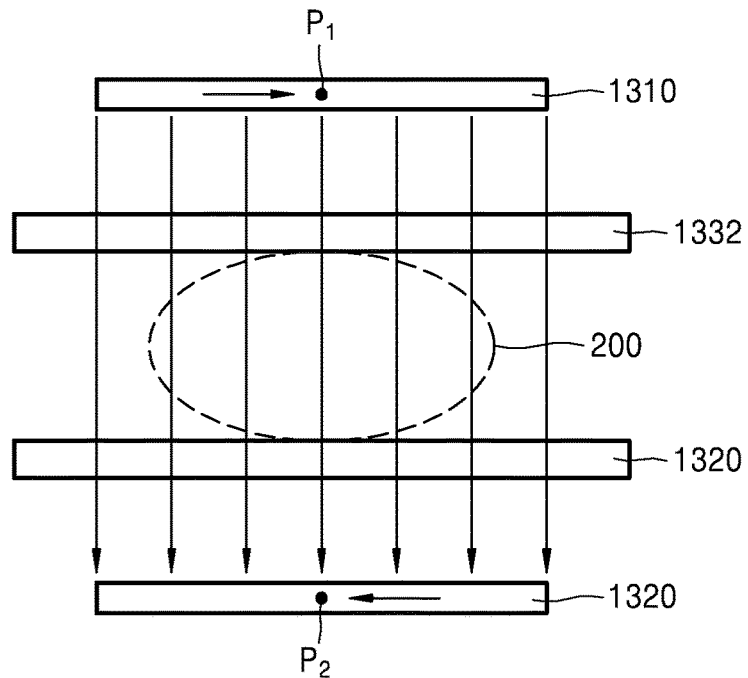
Figure 14C:
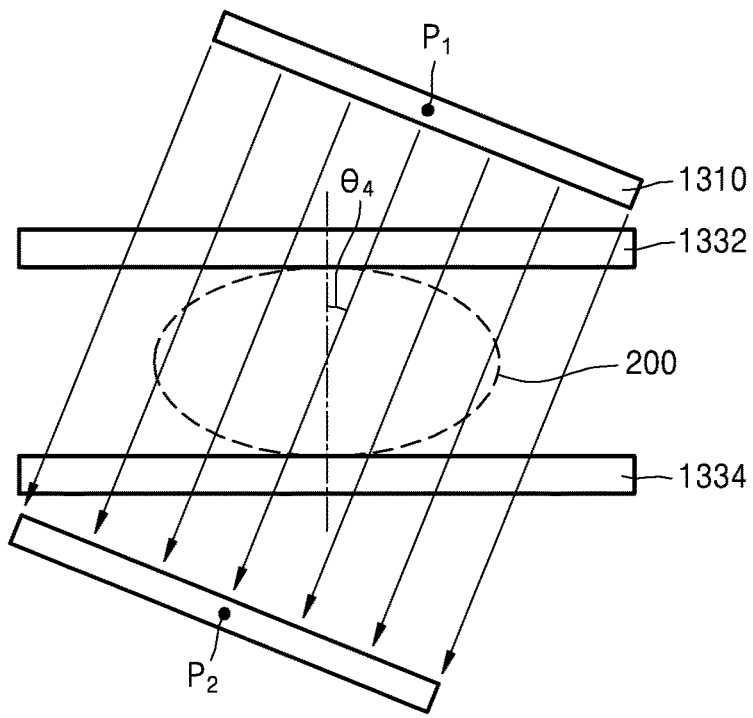

The X-ray detector 1320 may detect an X-ray by moving to correspond to a position of the X-ray generator 1310. FIGS. 14A through 14C are diagrams for explaining an X-ray photographing method which may be used to acquire a tomography image according to another exemplary embodiment.

Referring to FIG. 14A, when the X-ray generator 1310 is disposed on a left upper portion of the object 200, the X-ray generator 1310 may rotate with respect to the center axis P1 thereof such that an X-ray may be radiated in an inclined fashion to the object 200. In this regard, the X-ray detector 1320 may also move to face the X-ray generator 1310. For example, the X-ray detector 1320 may move to be disposed on a right lower portion of the object 200 and rotate with respect to a center axis P2 of the X-ray detector 1320 such that the X-ray generator 1310 and the X-ray detector 1320 may be disposed in parallel to each other. The X-ray generator 1310 may radiate an X-ray at a first radiation angle θ3 to the object 200, and thus, an X-ray photographing apparatus may photograph a first image of the object 200.

Referring to FIG. 14B, the X-ray generator 1310 may move to be disposed on the object 200. Furthermore, the X-ray generator 1310 may adjust its posture such that the X-ray generator 1310 may be disposed in parallel to the object 200. In this regard, the X-ray detector 1320 may also move. For example, the X-ray detector 1320 may move to be disposed under the object 200 and rotate with respect to the center axis P2 thereof such that the X-ray generator 1310, the object 200, and the X-ray detector 1320 may be disposed in parallel to each other. The X-ray generator 1310 may vertically radiate an X-ray to the object 200, and thus, the X-ray photographing apparatus may acquire a second image of the object 200.

Referring to FIG. 14C, the X-ray generator 1310 may move to a right upper portion of the object 200 and adjust its posture such that an X-ray is radiated in an inclined fashion to the object 200. In this regard, the X-ray detector 1320 may also move to be disposed in parallel to the X-ray generator 1310. For example, the X-ray detector 1320 may move to be disposed on a left lower portion of the object 200 and rotate with respect to the center axis P2 thereof such that the X-ray generator 1310, the object, 200, and the X-ray detector 1320 may be disposed in parallel to each other. The X-ray generator 1310 may radiate an X-ray at a second radiation angle θ4 to the object 200, and thus, the X-ray photographing apparatus may acquire a third image of the object 200.

As described above, the X-ray generator 1310 may move to vary a radiation angle of an X-ray and radiate the X-ray to the object 200, thereby simplifying a photographing process for acquiring a tomography image.

Furthermore, the X-ray generator 1310 and the X-ray detector 1320 may rotate, and thus, photographing may be performed to acquire the tomography image.

Figure 15:
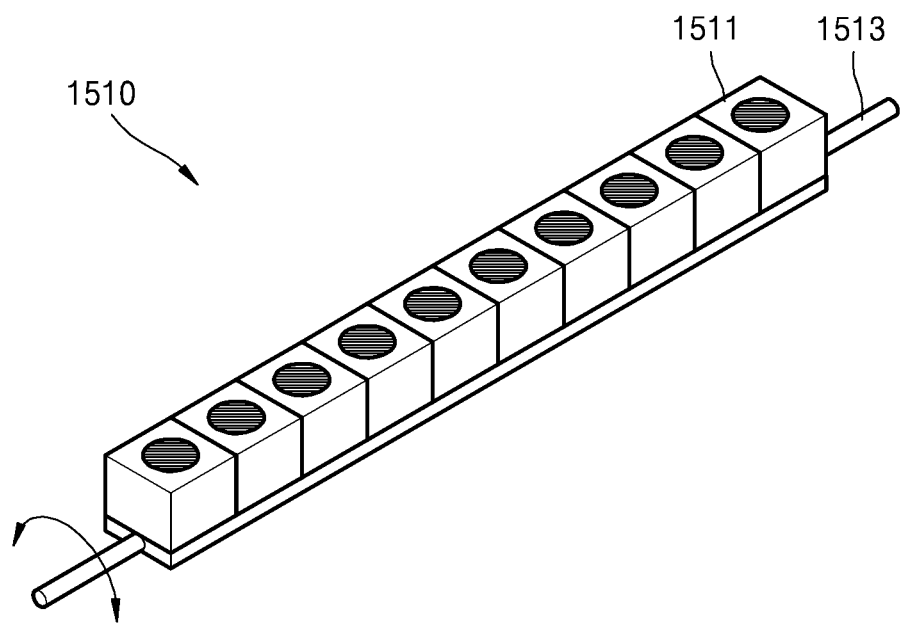
FIG. 15 is a schematic diagram of an X-ray generator according to an exemplary embodiment.

FIG. 15 is a schematic diagram of an X-ray generator 1510 according to an exemplary embodiment. Referring to FIG. 15, the X-ray generator 1510 according to an exemplary embodiment may include a plurality of X-ray generation units 1511 provided in one dimension and a rotation unit (e.g., rotator) 1513 that supports and rotates the X-ray generation units 1511. The X-ray generator 1510 may include a driver (not shown) that drives the rotation unit 1513. If the rotation unit 1513 rotates at a predetermined time interval, the X-ray generation units 1511 disposed on the rotation unit 1513 may radiate an X-ray to an object at different radiation angles at the predetermined time interval. An X-ray detector may include a rotation unit, similar to the X-ray generator 1510.

Figure 16A:
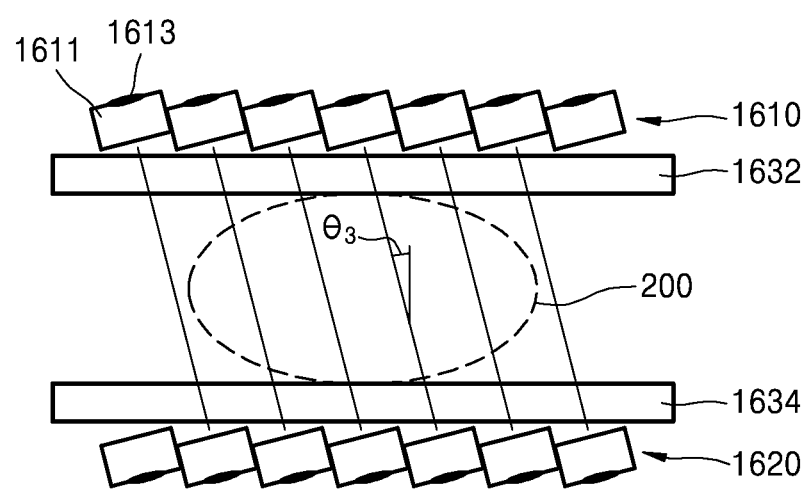
FIGS. 16A through 16C are diagrams for explaining an X-ray photographing method which may be used to acquire a tomography image according to another exemplary embodiment.
Figure 16B:
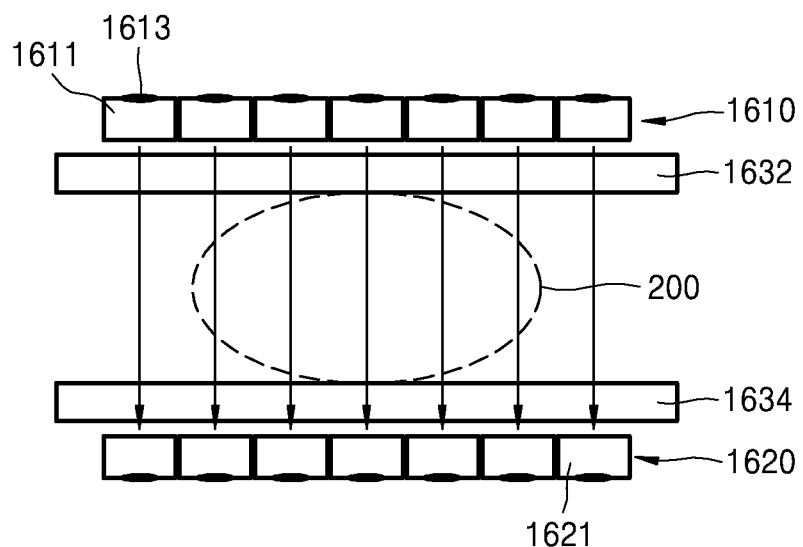
Figure 16C:
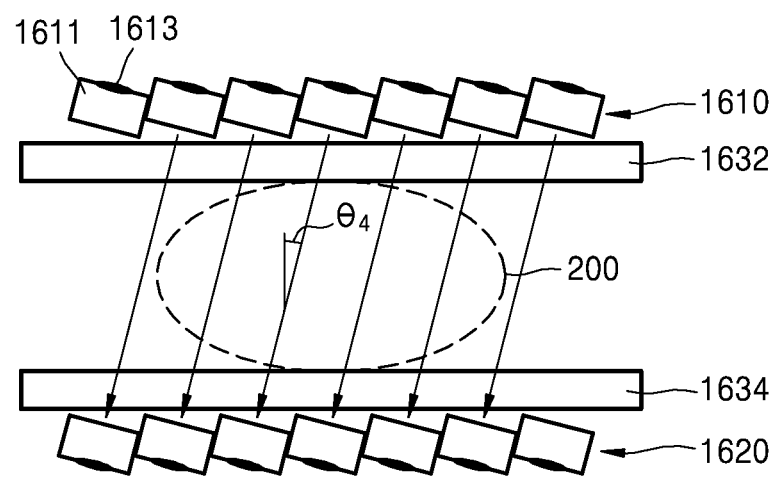

FIGS. 16A through 16C are diagrams for explaining an X-ray photographing method so as to acquire a tomography image according to another exemplary embodiment.

Referring to FIG. 16A, a rotation unit 1613 may rotate such that each X-ray generation unit 1613 of an X-ray generator 1610 may radiate an X-ray to the object 200 at the first radiation angle θ3 at a first time. For example, the rotation unit 1613 may rotate in a counterclockwise direction at the first time. The X-ray generator 1610 may radiate the X-ray to the object 200 at the first radiation angle θ3, and thus, an X-ray photographing apparatus may acquire a first image of the object 200.

Referring to FIG. 16B, each X-ray generation unit 1611 rotates in a clockwise direction at a second time after a predetermined time elapses and then the X-ray generator 1610 may vertically radiate an X-ray to the object 200. The X-ray photographing apparatus may acquire a second image of the object 200. Furthermore, referring to FIG. 16C, each of the X-ray generation units 1611 rotates in a clockwise direction at a third time after a predetermined time elapses and then the X-ray generator 1610 may vertically radiate an X-ray to the object 200 at the second radiation angle θ4. The X-ray photographing apparatus may acquire a third image of the object 200. In this regard, X-ray detection units 1621 may rotate similar to the X-ray generation units 1611 to detect an X-ray.

As described above, an X-ray radiation angle may be changed by rotating only the X-ray generation units 1611, thereby simplifying a photographing process for acquiring the tomography image.

Figure 17:
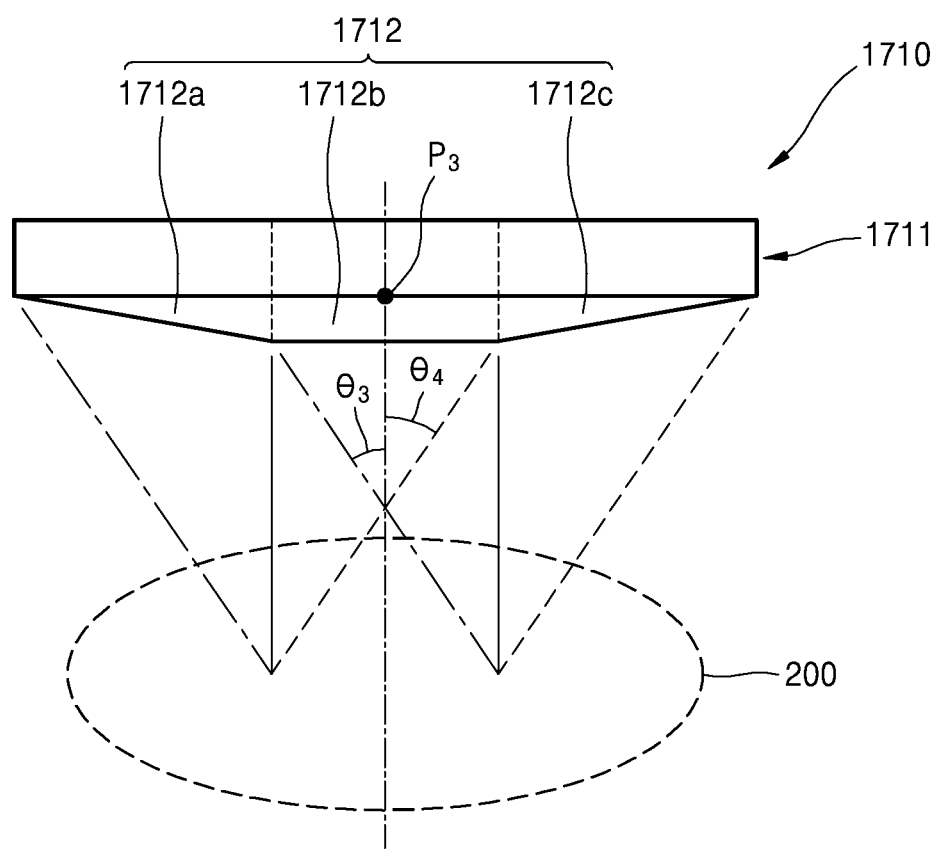
FIG. 17 is a schematic diagram of an X-ray generator used to acquire a tomography image according to an exemplary embodiment.

Furthermore, a shape of an anode electrode among the X-ray generation units 1611 may be used to change the X-ray radiation angle with respect to the object 200. FIG. 17 is a schematic diagram of an X-ray generator 1710 used to acquire a tomography image according to an exemplary embodiment. Referring to FIG. 17, the X-ray generator 1710 may include an anode electrode 1712 that emits an X-ray due to collisions between a plurality of electron emission devices 1711 that are independently driven and electrons. The anode electrode 1712 may have a different thickness with respect to a center axis P3 of the X-ray generator 1710. For example, if the anode electrode 1712 is divided into three regions, a thickness of the first region 1712a increases in a direction moving from an edge towards the center axis P3 of the X-ray generator 1710, a thickness of a second region 1712b is uniform, and a thickness of a third region 1712c decreases as the third region 1712c decreases in a direction moving away from the center axis P3 of the X-ray generator 1710 towards an edge. Thus, an X-ray from the first region 1712a is radiated to the object 200 at the first radiation angle θ3, an X-ray from the second region 1712b may be vertically radiated to the object 200, and an X-ray from the third region 1712c may be radiated to the object 200 at the second radiation angle θ4.

If the electron emission device 1711 corresponding to the first region 1712a emits electrons at a first time, the X-ray generated in the first region 1712a may be radiated to the object 200 at the first radiation angle θ3. If the electron emission device 1711 corresponding to the second region 1712b emits electrons at a second time, the X-ray generated in the second region 1712b may be vertically radiated to the object 200. If the electron emission device 1711 corresponding to the third region 1712c emits electrons at a third time, the X-ray may be generated in the third region 1712c. The X-ray generated in the third region 1712c may be radiated to the object 200 at the second radiation angle θ4. Thus, an X-ray photographing apparatus may perform X-ray photographing to acquire the tomography image by using a shape of the anode electrode 1712.

The X-ray photographing to acquire the tomography image may be performed three times, according to an exemplary embodiment. However, this example is simply for convenience of description, and X-ray photographing may be performed two or more times to acquire the tomography image according to other exemplary embodiments.

The X-ray photographing apparatus according to the present exemplary embodiment may further include a sensing unit that senses the object 200. The sensing unit may include a plurality of sensors. Each sensor may sense an existence of the object 200 and determine a location of the object 200 based on results of sensing by all the sensors. The sensors may be light sensors (in particular, illumination sensors), touch sensors, etc. In particular, when the sensors are touch sensors, the sensors may be formed as a single pad, e.g., a touch pad.

Figure 18A:
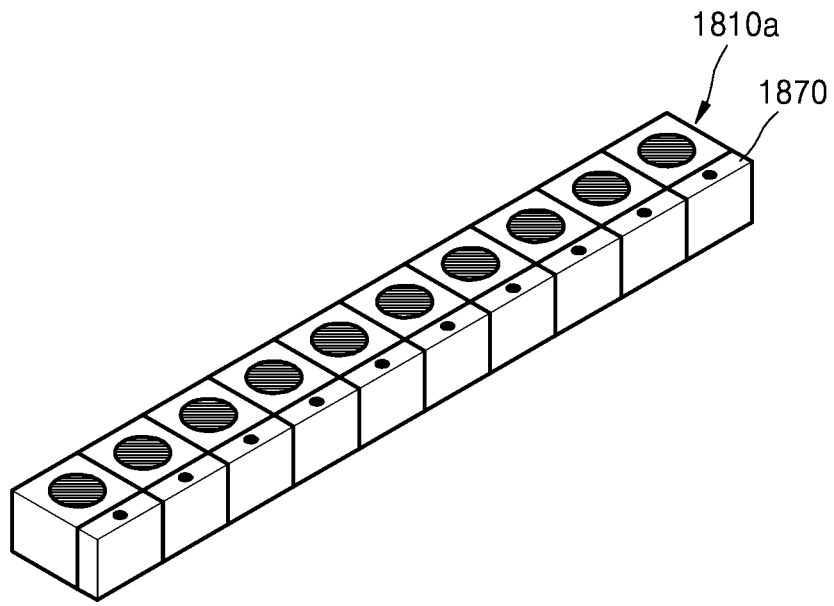
FIGS. 18A and 18B are schematic diagrams of X-ray generators including a plurality of sensors according to an exemplary embodiment.
Figure 18B:
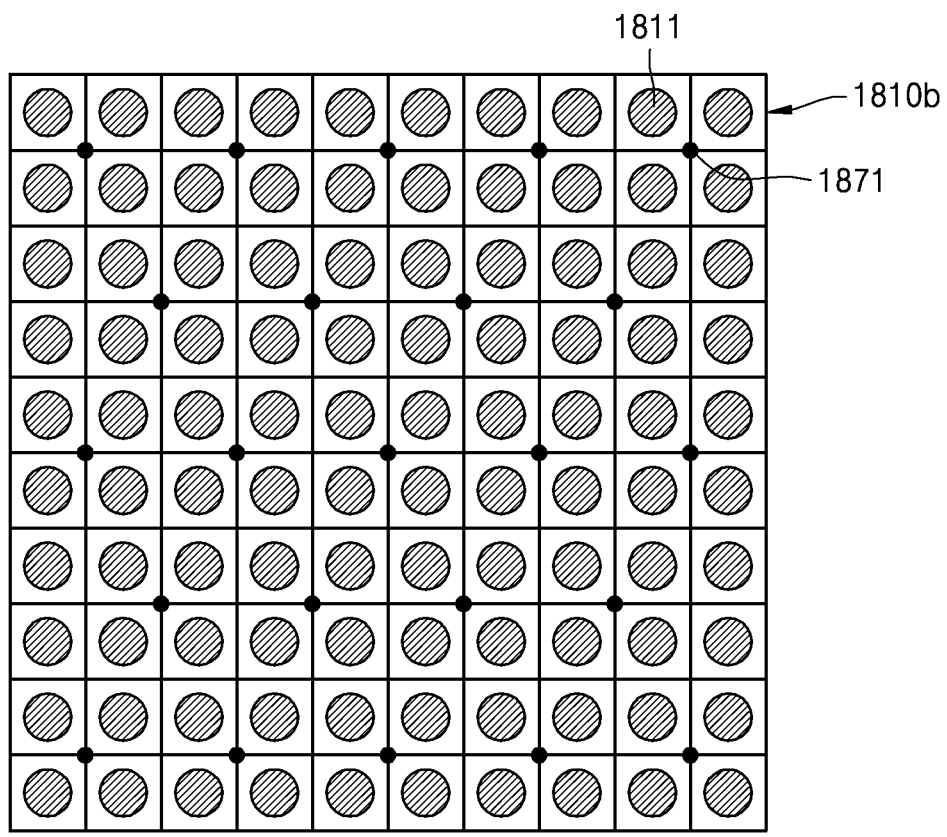

FIGS. 18A and 18B are schematic diagrams of X-ray units 1810a and 1810b including a plurality of sensors 1871 according to an exemplary embodiment. The X-ray units 1810a, 1810b, and 1811 may be implemented as X-ray generators or X-ray detectors. The sensors 1871 may be provided to be integrated with the X-ray units 1810a and 1810b. Referring to FIG. 18A, a one dimensional sensor array 1870 is provided at a side of the one dimensional X-ray units 1810a so that the one dimensional X-ray unit 1810a and the one dimensional sensor array 1870 may be integrated. Alternatively, referring to FIG. 18B, the sensors 1871 may be provided to be spaced apart from each other on a two dimensional X-ray unit 1810b. The sensors 1871 may be disposed not to overlap with X-ray units 1811. In FIG. 18B, the sensors 1871 are disposed on regions in which four X-ray units 1811 are adjacent. In particular, the sensors 1871 may be disposed on the same plane of the X-ray units 1810a and 1810b as an anode electrode (not shown). Thus, an X-ray traveling path may not be influenced by the sensors 1871. However, the exemplary embodiments are not limited thereto. According to an exemplary embodiment, locations of the sensors 1871 may be varied in many different ways, as long as the X-ray traveling path and the sensors 1871 do not overlap with each other.

Although the sensors 1871 are exemplarily shown as being disposed on the entire regions in which the X-ray units 1810a and 1810b are disposed, the exemplary embodiments are not limited thereto. When a size and location of an object are generally known, the sensors 1871 may not be provided in a region in which the object is necessarily disposed or in a region in which there is no possibility that the object is to be disposed. The sensors 1871 may be focused in a region corresponding to a boundary of the object. The sensors 1871 provided on the X-ray units 1810a and 1810b may be light sensors.

Although the sensors 1871 are exemplarily shown as being integrally formed with the X-ray units 1810a and 1810b in FIGS. 18A and 18B, the exemplary embodiments are not limited thereto. The sensors 1871 may be integrally formed with X-ray detectors. For example, when X-ray detectors are one dimensional X-ray detectors, the sensors 1871 may be disposed to contact the X-ray detectors. When the X-ray detectors are two dimensional X-ray detectors, the sensors 1871 may be disposed between the X-ray detectors.

Figure 19A:
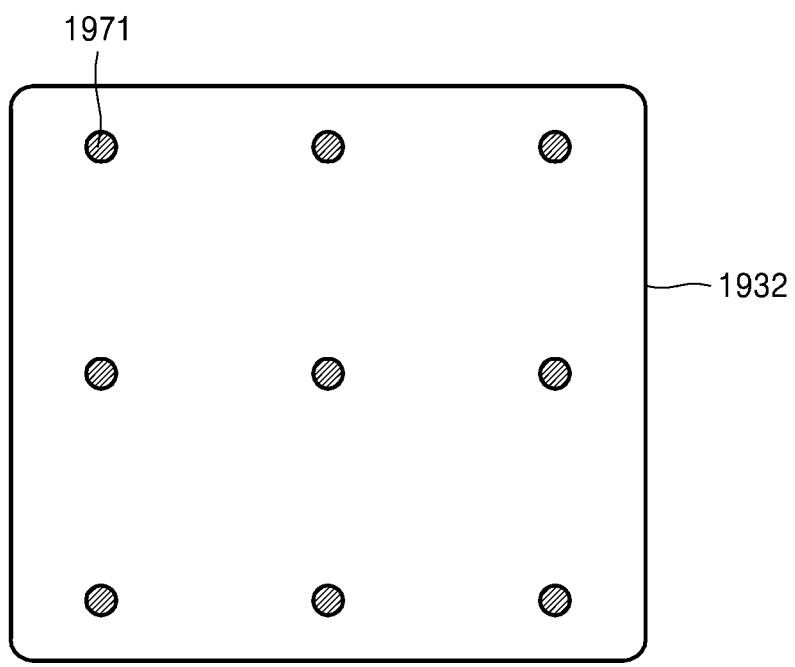
FIGS. 19A and 19B illustrate a panel on which sensors are disposed according to an exemplary embodiment.
Figure 19B:
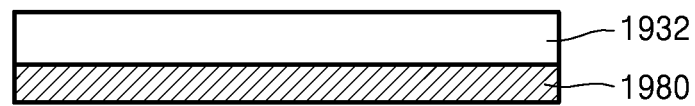

FIGS. 19A and 19B illustrate a panel 1932 on which sensors 1971 are disposed according to an exemplary embodiment. Referring to FIG. 19A, the sensors 1971 may be disposed on the panel 1932. If the sensors 1971 are disposed on an X-ray generator, when the X-ray generator does not cover an object, the X-ray generator should be moved in a horizontal direction to detect a location of the object. However, since the panel 1932 covers the object, when the sensors 1971 are disposed on the panel 1932, the object may be more easily detected. The sensors 1971 may be disposed on a surface of the panel 1932 facing the X-ray generator or on a surface of the panel 1932 facing the object. The sensors 1971 disposed on the panel 1932 may be light sensors, touch sensors, etc. When the sensors 1971 are disposed on the panel 1932, the sensors 1971 may be formed of a transparent material so as to minimize diffusion of an X-ray or absorption by the sensors 1971. In particular, when the sensors 1971 are touch sensors, the sensors 1971 may be implemented as a touch pad 1980.

Figure 20:
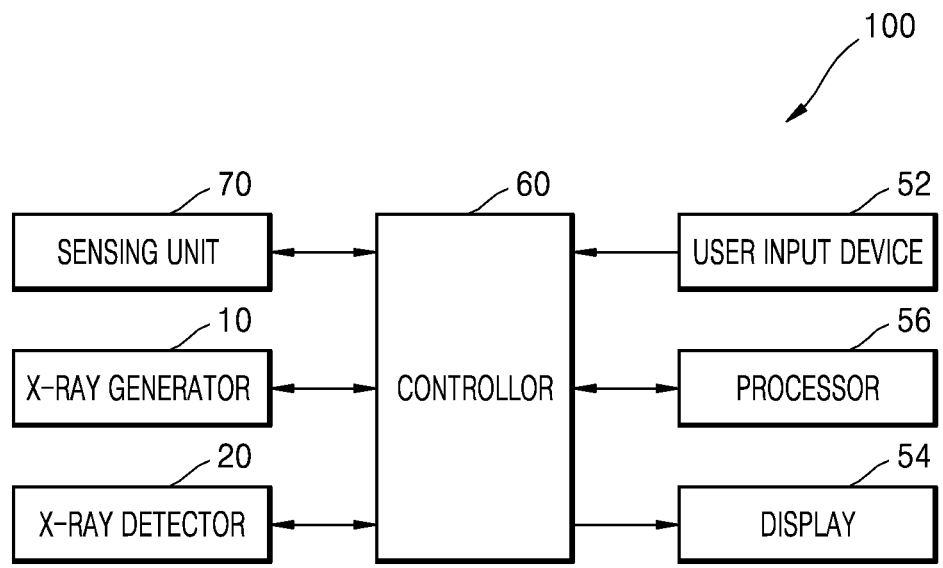
FIG. 20 is a block diagram of an X-ray photographing apparatus according to an exemplary embodiment.

FIG. 20 is a block diagram of the X-ray photographing apparatus 100 of FIG. 1 according to an exemplary embodiment. Referring to FIG. 20, the X-ray photographing apparatus 100 may include an X-ray generator 10, an X-ray detector 20, the user input device 52, a display 54, a processor 56, and a controller 60. The X-ray photographing apparatus 100 may further include a sensing unit 70 that senses an object.

The X-ray generator 10 radiates an appropriate X-ray to the object as described above. Since the X-ray generator 10 has been described above, a description thereof will not be repeated here. The X-ray detector 20 detects the X-ray that is transmitted to the object. Since the process of the X-ray detector 20 detecting the X-ray has been described above, a description thereof will not be repeated here.

The user input device 52 receives input of an X-ray photographing command from a user such as a medical expert. Information regarding a command to change a location of the X-ray generator 10, a parameter adjustment command to vary an X-ray spectrum, a command regarding a main body of the X-ray photographing apparatus 100 or a movement of the X-ray generator 10, and many other types of commands received from the user, may be transmitted to the controller 60. The controller 60 controls elements included in the X-ray photographing apparatus 100 according to a user command.

The processor 56 receives an electrical signal corresponding to the X-ray detected by the X-ray detector 20. The processor 56 may preprocess the electrical signal to acquire an image. In this regard, preprocessing may include at least one of offset compensation, algebra conversion, X-ray dose compensation, sensitivity compensation, and beam hardening. The image may be a tomography image.

The processor 56 may preprocess the electrical signal corresponding to the detected X-ray to acquire the image. The processor 56 may preprocess an electrical signal corresponding to the detected X-ray to acquire transparent data and reconfigure the acquired transparent data for each radiation angle to acquire the tomography image.

Configurations, locations and types of the sensing unit 70 have been described above, and thus a detailed description thereof will not be repeated here. Each sensor included in the sensing unit 70 may sense an existence of the object and transmit a result of the sensing to the controller 60. Thus, the controller 60 may determine a location of the object by using results of the sensing by the sensors. The controller 60 may control the X-ray generator 10 to enable an X-ray generation unit of the X-ray generator 10 corresponding to the location of the object to generate an X-ray. Furthermore, the controller 60 may control the X-ray detector 20 to enable an X-ray detection unit of the X-ray detector 20 corresponding to the location of the object to detect an X-ray that is transmitted to the object.

According to an exemplary embodiment, only some of the X-ray generation units operate to photograph the object, thereby reducing an X-ray radiation dose. Furthermore, only some of the X-ray detection units operate, and thus, a lifetime of the X-ray detector 20 may be increased, thereby simplifying signal processing.

Figure 21:
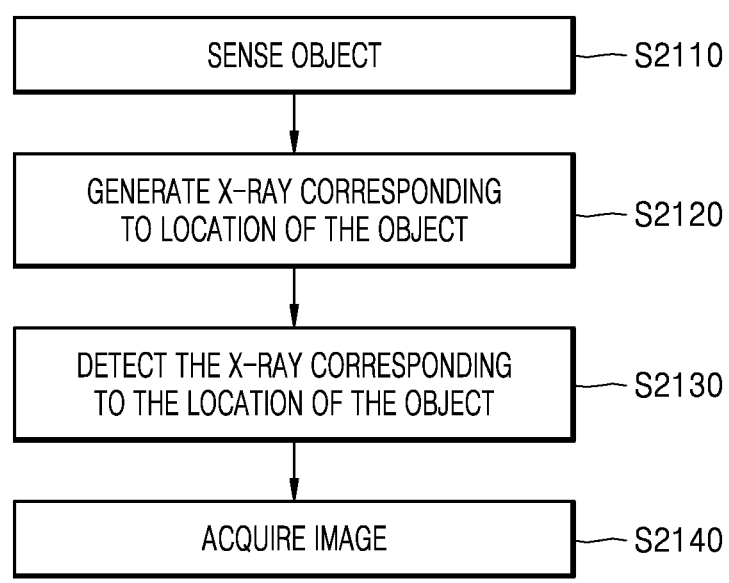
FIG. 21 is a flowchart of an X-ray photographing method according to an exemplary embodiment.

An X-ray photographing method using the sensing unit 70 will now be described. FIG. 21 is a flowchart of an X-ray photographing method according to an exemplary embodiment. Referring to FIG. 21, the sensing unit 70 senses the object 200 at operation S2110. If the object 200 is disposed between the first panel 32 and the second panel 34 of the X-ray photographing apparatus 100 of FIG. 1, the X-ray photographing apparatus 100 may move at least one of the first panel 32 and the second panel 34 according to a user command to compress the object 200. If the object 200 contacts the first panel 32 and the second panel 34 or is pressed by the first panel 32 and the second panel 34, each sensor included in the sensing unit 70 may sense an existence of the object 200. For example, when sensors are illumination sensors, the sensors may sense whether the object 200 exists based on an illumination change, and when the sensors are touch sensors, the sensors may sense whether the object 200 exists according to whether the touch sensors are touched. A result of the sensing by each sensor is transmitted to the controller 60.

The controller 60 may control the X-ray generator 10 to enable an X-ray generation unit of the X-ray generator 10 corresponding to a location of the object 200 to generate an X-ray by using results of the sensing by the sensing unit 70 at operation S2120. The controller 60 may determine the location of the object 200 from the result of the sensing by each sensor. For example, the location of the object 200 may be determined from locations of the sensors that detect the illumination change and whether the sensors are touched. The location of the object 200 may be determined to be slightly greater than locations of the sensors. The controller 60 may control the X-ray generation unit of the X-ray generator 10 corresponding to the location of the object 200 to generate the X-ray. An X-ray generation method may vary according to sizes of an X-ray test area and an X-ray generation area, and according to whether an image that is to be photographed is a simple image or a tomography image. Since these features have been described above, a detailed description thereof will not be repeated here.

The controller 60 may control the X-ray detector 20 to enable an X-ray detection unit of the X-ray detector 20 corresponding to the location of the object to detect the X-ray at operation S2130. An X-ray detection method may vary according to sizes of the X-ray test area and the X-ray generation area, and according to whether the image that is to be photographed is the simple image or the tomography image. Since these features have been described above, a detailed description thereof will not be repeated here. If only the X-ray detection unit of the X-ray detector 20 corresponding to the location of the object detects the X-ray, the X-ray diffused by being transmitted to the object 200 is detected, thereby blocking noise.

Then, the processor 56 may receive an electrical signal corresponding to the X-ray detected by the X-ray detection unit to acquire an image at operation S2140. The acquired image may be displayed on the display 54.

Although the above description exemplarily describes that the sensing unit 70 senses the object 200, and the X-ray photographing apparatus 100 operates according to a result of the sensing, the exemplary embodiments are not limited thereto. For example, when the sensing unit 70 is not included in the X-ray photographing apparatus 100, the X-ray photographing apparatus 100 may perform photographing as described with reference to FIGS. 11A through 16C.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the exemplary embodiments as defined by the following claims.

What is claimed is:

1. An X-ray photographing apparatus comprising:
   an X-ray generator including a plurality of X-ray generation units configured to generate X-rays based on a location of an object and to emit X-rays towards the object;
   an X-ray detector configured to face the X-ray generator and to detect the X-rays that are transmitted through the object; and
   a plurality of sensors configured to sense the object,
   wherein two of the plurality of sensors are spaced apart from each other by interposing at least one of the X-ray generation units therebetween, and
   wherein the two sensors are touch sensors configured to sense the location of the object based on contact with the object.

2. The X-ray photographing apparatus of claim 1, wherein X-ray generation units corresponding to the location of the object, among the plurality of X-ray generation units, are configured to generate the X-ray.

3. The X-ray photographing apparatus of claim 1, wherein the X-ray detector comprises a plurality of X-ray detection units, and X-ray detection units corresponding to the location of the object, among the plurality of X-ray detection units, are configured to detect the X-ray.

4. The X-ray photographing apparatus of claim 1, wherein the X-ray detector comprises a plurality of X-ray detection units, and the plurality of X-ray generation units and the plurality of X-ray detection units are provided in one dimension or in two dimensions.

5. The X-ray photographing apparatus of claim 1, wherein each of the plurality of sensors is configured to sense the object.

6. The X-ray photographing apparatus of claim 1, further comprising: a controller configured to determine at least one of the location of the object and a location of X-ray radiation by using results of sensing by the plurality of sensors.

7. The X-ray photographing apparatus of claim 1, wherein at least one of the plurality of sensors is disposed in a region that does not overlap with the plurality of X-ray generation units.

8. The X-ray photographing apparatus of claim 1, further comprising: a panel that is provided between the X-ray generator and the X-ray detector and that is configured to contact the object.

9. The X-ray photographing apparatus of claim 8, wherein the panel is configured to compress the object.

10. The X-ray photographing apparatus of claim 1, wherein at least one of the plurality of sensors comprises a light sensor.

11. The X-ray photographing apparatus of claim 10, wherein the light sensor comprises an illumination sensor.

12. The X-ray photographing apparatus of claim 1, wherein the plurality of X-ray generation units are configured to move away from or closer to the object.

13. The X-ray photographing apparatus of claim 1, wherein each of the plurality of X-ray generation units comprises:
   an electron emission device configured to emit electrons; and
   an anode electrode configured to emit X-rays using the electrons emitted by the electron emission device.

14. The X-ray photographing apparatus of claim 13, wherein at least one of the plurality of sensors is disposed on a same plane as the anode electrode.

15. An X-ray photographing method performed by an X-ray photographing apparatus, the X-ray photographing method comprising:
   sensing an object using a plurality of sensors which are integrally formed with a plurality of X-ray generation units, two of the sensors being spaced apart from each other by interposing at least one of the X-ray generation units therebetween;
   generating an X-ray by using an X-ray generation unit corresponding to a location of the object, from among the plurality of X-ray generation units; and
   detecting the X-ray transmitted through the object by using an X-ray detection unit corresponding to the location of the object, from among a plurality of X-ray detection units,
   wherein the two sensors are touch sensors configured to sense the location of the object based on contact with the object.

16. The X-ray photographing method of claim 15, further comprising: determining the location of the object by using a result of the sensing.

17. The X-ray photographing method of claim 15, wherein the detecting is performed by using at least one of a light sensor and one of the touch sensors.

18. The X-ray photographing apparatus of claim 1, wherein the plurality of sensors are integrally formed with the plurality of X-ray generation units.

19. An X-ray photographing apparatus comprising:
   an X-ray generator including a plurality of X-ray generation units to generate X-rays and to emit X-rays towards an object;
   an X-ray detector configured to face the X-ray generator and to detect X-rays that are transmitted through the object;
   a panel that is provided between the X-ray generator and the X-ray detector and that is configured to contact the object; and
   a plurality of sensors which are formed on the panel and which are configured to sense a location of the object,
   wherein the sensors are touch sensors configured to sense the location of the object based on contact with the object, and
   wherein, in response to at least one of the touch sensors sensing the location of the object, X-ray generation units corresponding to the sensed location of the object, among the plurality of X-ray generation units, generate the X-rays, and X-ray generation units other than the X-ray generation units corresponding to the sensed location of the object remain turned off.

* * * * *